US008598224B2

(12) United States Patent
Nelson et al.

(10) Patent No.: US 8,598,224 B2
(45) Date of Patent: *Dec. 3, 2013

(54) METHOD FOR TREATING CANNABINOID RECEPTOR RELATED DISEASES WITH CANNABINOID RECEPTOR LIGANDS

(75) Inventors: Derek W Nelson, Highland Park, IL (US); Jennifer M Frost, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 411 days.

This patent is subject to a terminal disclaimer.

(21) Appl. No.: 12/967,275

(22) Filed: Dec. 14, 2010

(65) Prior Publication Data

US 2011/0086838 A1    Apr. 14, 2011

Related U.S. Application Data

(62) Division of application No. 11/848,509, filed on Aug. 31, 2007, now Pat. No. 7,868,038.

(60) Provisional application No. 60/841,355, filed on Aug. 31, 2006.

(51) Int. Cl.
*A61K 31/381*    (2006.01)

(52) U.S. Cl.
USPC ........................................................ 514/443

(58) Field of Classification Search
USPC ........................................................ 514/443
See application file for complete search history.

(56) References Cited

U.S. PATENT DOCUMENTS

| 6,559,186 B1 | 5/2003 | Campbell |
| 7,868,038 B2 * | 1/2011 | Nelson et al. .................. 514/443 |
| 2008/0312435 A1 | 12/2008 | Saito et al. |

FOREIGN PATENT DOCUMENTS

| EP | 412404 A2 | 2/1991 |
| EP | 568096 A1 | 11/1993 |
| EP | 1219612 A1 | 7/2002 |
| FR | 2796643 A1 | 1/2001 |
| WO | WO2005023818 A2 | 3/2005 |
| WO | WO2005058887 A1 | 6/2005 |
| WO | WO2006051704 A1 | 5/2006 |
| WO | WO2006070106 A1 | 7/2006 |

OTHER PUBLICATIONS

Ambartsumova, et al., "Effect of Various Factors on the Reaction of 2-Aminobenzothiazoles with Propylene Oxide," Chemistry of Heterocyclic Compounds, 2002, vol. 38 (8), pp. 994-999.
Ansell, et al., "The Synthesis of (+/−)-10a-Homo-11a-Carbathromboxane A1, a Stable Thromboxane A Analogue," Journal of Chemical Society Perkin Trans, 1984, pp. 1061-1068.
Arevalo-Martin, et al., "Therapeutic Action of Cannabinoids in a Murine Model of Multiple Sclerosis," Journal of Neuroscience, 2003, vol. 23 (7), pp. 2511-2516.

Baker, et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Benito, et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.
Benito, et al., "Cannabinoid CB2 Receptors and Fatty Acid Amide Hydrolase are Selectively Overexpressed in Neuritic Plaque-Associated Glia in Alzheimer's Disease Brains," Journal of Neuroscience, 2003, vol. 23 (35), pp. 11136-11141.
Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle, et al., "Osteoclast Differentiation and Activation," Nature, 2003, vol. 423 (6937), pp. 337-342.
Brennan, et al., "Characterization of a Rat Model of Incisional Pain," Pain, 1996, vol. 64, pp. 493-450.
Buckley, et al., "Immunomodulation by Cannabinoids is Absent in Mice Deficient for the Cannabinoid CB2 Receptor," European Journal of Pharmacology, 2000, vol. 396, pp. 141-149.
Carlisle, et al., "Differential Expression of the CB2 Cannabinoid Receptor by Rodent Macrophages and Macrophage-like Cells in Relation to Cell Activation," International Immunopharmacology, 2002, vol. 2, pp. 69.
Carrier, et al., "Endocannabinoids in Neuroimmunology and Stress," Current Drug Targets CNS and Neurological Disorders, 2005, vol. 4, pp. 657-665.
Casanova, et al., "Inhibition of Skin Tumor Growth and Angiogenesis in vivo by Activation of Cannabinoid Receptors," Journal of Clinical Investigation, 2003, vol. 111 (1), pp. 43-50.
Chaplan, et al., "Quantitative Assessment of Tactile Allodynia in the Rat Paw," Journal of Neuroscience Methods, 1994, vol. 53, pp. 55-63.
Cichewicz, D., "Synergistic Interactions Between Cannabinoid and Opioid Analgesics," Life Sciences, 2004, vol. 74 (11), pp. 1317-1324.
Clayton, et al., "CB1 and CB2 Cannabinoid Receptors are Implicated in Inflammatory Pain," Pain, 2002, vol. 96 (3), pp. 253-260.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Dixon, W., "Efficient Analysis of Experimental Observations," Annual Review of Pharmacology and Toxicology, 1980, vol. 20, pp. 441-462.

(Continued)

*Primary Examiner* — Bernard Dentz
(74) *Attorney, Agent, or Firm* — Lisa V. Mueller; Michael Best & Friedrich LLP

(57) ABSTRACT

The present invention relates to thiophene containing compounds of formula (I)

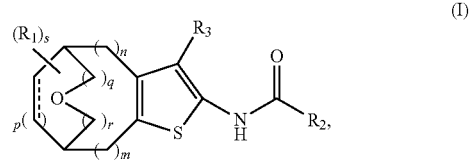

wherein m, n, p, q, r, s, $R_1$, $R_2$, and $R_3$ are as defined in the description. Included also are pharmaceutical compositions comprising such compounds, and methods for treating conditions and disorders using such compounds and pharmaceutical compositions.

1 Claim, No Drawings

(56) References Cited

OTHER PUBLICATIONS

Dorsch, et al., "The Preparation of Benzoylacetic Ester and Some of its Homologs," Journal of the American Chemical Society, 1932, vol. 54, pp. 2960-2964.

Fattori, et al., "The Demjanov and Tiffeneau-Demjanov One-Carbon Ring Enlargements of 2-Aminomethyl-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.

Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.

Galiégue, et al., "Expression of Central and Peripheral Cannabinoid Receptors in Human Immune Tissues and Leukocyte Subpopulations," European Journal of Biochemistry, 1995, vol. 232 (1), pp. 54-61.

Golech, et al., "Human Brain Endothelium: Coexpression and Function of Vannilloid and Endocannabinoid Receptors," Molecular Brain Research, 2004, vol. 132 (1), pp. 87-92.

Greene, et al., "Protection for the Amino group," Protective Groups in Organic Synthesis, 1999, Third Edition, pp. 494-653.

Greene, et al., Protective Groups in Organic Synthesis, 3rd Edition, John Wiley and Sons, Inc., 1999, Table of Contents.

Grotenhermen, et al., "IACM 2nd Conference on Cannabinoids in Medicine," Expert Opinion in Pharmacotherapy, 1976, vol. 4 (12), pp. 2367-2371.

Hands, et al., "HU-308: A Specific Agonist for CB 2, a Peripheral Cannabinoid Receptor," Proceedings of the National Academy of Science, 1999, vol. 96, pp. 14228-14233.

Hargreaves, et al., "A New and Sensitive Method for Measuring Thermal Nociception in Cutaneous Hyperalgesia," Pain, 1988. 32 (1), pp. 77-88.

Hohmann, et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.

Ibrahim, et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.

Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.

Ihenetu, et al , "Inhibition of Interleukin-8 Release in the Human Colonic Epithelial Cell Line HT-29 by Cannabinoids," European Journal of Pharmacology, 2003, vol. 458 (1-2), pp. 207-215.

International Search Report and Written Opinion for Application No. PCT/US2007/077320, mailed on Feb. 7, 2008, 12 pages.

International Search Report for Application No. PCT/US 2007/069921, mailed on Nov. 27, 2008, 4 pages.

International Search Report for Application No. PCT/US2007/0077321, mailed on Feb. 1, 2008, 3 pages.

Julien, et al., "Antifibrogenic Role of the Cannabinoid Receptor CB2 in the Liver," Gastroenterology, 2005, vol. 128, pp. 742-755.

Karsak, et al., "Cannabinoid Receptor Type 2 Gene is Associated with Human Osteoporosis," Human Molecular Genetics, 2005, vol. 14 (22), pp. 3389-3396.

Kim, et al., "An Experimental Model for Peripheral Neuropathy Produced by Segmental Spinal Nerve Ligation in the Rat," Pain, 1992, vol. 50 (3), pp. 355-363.

Kreutzberg, et al., "Microglia: A Sensor for Pathological Events in the CNS," Trends in Neuroscience, 1996, vol. 19, pp. 312-318.

Lepicier, et al., "Endocannabinoids Protect the Rat Isolated Heart Against Ischaemia," British Journal of Pharmacology, 2003, vol. 139, pp. 805-815.

Lotersztajn, et al., "Hepatic Fibrosis: Molecular Mechanisms and Drug Targets," Annual Review of Pharmacology and Toxicology, 2005, vol. 45, pp. 605-628.

Malan, et al., "CB2 Cannabinoid Receptor-Mediated Peripheral Antinociception," Pain, 2001, vol. 93, pp. 239-245.

Maresz, et al., "Modulation of the Cannabinoid CB2 Receptor in Microglial Cells in Response to Inflammatory Stimuli," Journal of Neurochemistry, 2005, vol. 95, pp. 437-445.

Mathison, et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.

McKallip, et al., "Targeting CB2 Cannabinoid Receptors as a Novel Therapy to Treat Malignant Lymphoblastic Disease," Blood, 2002, vol. 15 (2), pp. 627-634.

Molina-Holgado, et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.

Nackley, et al., "Selective Activation of Cannabinoid CB2 Receptors Suppresses Spinal for Protein Expression and Pain Behavior in a Rat Model of Inflammation," Neuroscience, 2003, vol. 119, pp. 747-757.

Ni, et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.

Nunez, et al., "Cannabinoid CB2 Receptors Are Expressed by Perivascular Microglial Cells in the Human Brain: An Immunohistochemical Study," Synapse, 2004, vol. 53, pp. 208-213.

Partch, et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.

Patel, et al , "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.

Pertwee, R., "Cannabinoids and Multiple Sclerosis," Pharmacology & Therapeutics, 2002, vol. 95, pp. 165-174.

Poste, et al., "Lipid Vesicles as Carriers for Introducing Biologically Active Materials into Cells," Methods in Cell Biology, 1976, vol. 14, pp. 33-71.

Quartilho, et al , "Inhibition of Inflammatory Hyperalgesia by Activation of Peripheral CB2 Cannabinoid Receptors," Anesthesiology, 2003, vol. 99, pp. 955-960.

Ralston, S., "Genetic Determinants of Susceptibility to Osteoporosis," Current Opinion in Pharmacology, 2003, vol. 3, pp. 286-290.

Ralston, S., "Regulation of Bone Mass, Bone Loss and Osteoclast Activity by Cannabinoid Receptors," Nature Medicine, 2005, vol. 11 (7), pp. 774-779.

Ramirez, et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.

Sabnis, et al., "2-Aminothiophenes by the Gewald Reaction," Journal of Heterocyclic Chemistry, 1999, vol. 36, pp. 333-345.

Sanchez, et al , "Inhibition of Glioma Growth in Vivo by Selective Activation of the CB2 Cannabinoid Receptorl," Cancer Research, 2001, vol. 61, pp. 5784-5789.

Steffens, et al., "Low Dose Oral Cannabinoid Therapy Reduces Progression of Atherosclerosis in Mice," Nature, 2005, vol. 434, pp. 782-786.

Valenzano, et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.

Walter, et al., "Cannabinoids and Neuroinflammation," British Journal of Pharmacology, 2004, vol. 141 (5), pp. 775-785.

Warhurst, et al., "Interferon Gamma Induces Differential Upregulation of Alpha and Beta Chemokine Secretion in Colonic Epithelial Cell Lines," Gut, 1998, vol. 42 (2), pp. 208-213.

Watkins, et al., "Glial Activation: A Driving Force for Pathological Pain," Trends in Neuroscience, 2001, vol. 24 (8), pp. 450-455.

(56) References Cited

OTHER PUBLICATIONS

Werbel, et al., "1-Alkyl-3-(3-alkyl-5-nitro-4-thiazolin-2-ylidene)ureasa and Related Compounds as Schistosomicides," Journal of Medicinal Chemistry, 1972, vol. 15 (9), pp. 955-963.

Weyer, et al., "Blutzuckersenkende Chinolin-8-Carboxamidoalkyl-Benzol Sulfonamid Derivate," Arzneimittel-Forschung, 1974, vol. 24 (3), pp. 269-275.

Williams, et al., "Central Nervous System Perivascular Cells Are Immunoregulatory Cells that Connect the CNS with the Peripheral mune System," Journal Of Glia, 2001, vol. 36 (2), pp. 156-164.

Wright, et al., "Differential Expression of Cannabinoid Receptors in the Human Colon: Cannabinoids Promote Epithelial Wound Healing," Gastroenterology, 2005, vol. 129 (2), pp. 437-453.

Yoshihara S, et al., "Cannabinoid Receptor Agonists Inhibit Sensory Nerve Activation in Guinea Pig Airways," American Journal of Respiratory and Critical Care Medicine, 2004, vol. 170 (9), pp. 941-946.

Yoshihara, et al., "Endogenous Cannabinoid Receptor Agonists Inhibit Neurogenic Inflammations in Guinea Pig Airways," Allergy and Immunology, 2005, vol. 138, pp. 80-87.

Yoshihara, et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

Zimmer, et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.

* cited by examiner

METHOD FOR TREATING CANNABINOID RECEPTOR RELATED DISEASES WITH CANNABINOID RECEPTOR LIGANDS

This application is a divisional application of U.S. patent application Ser. No. 11/848,509 filed on Aug. 31, 2007, which claims priority to U.S. patent application Ser. No. 60/841,355, filed Aug. 31, 2006, and are incorporated herein by reference in their entirety.

TECHNICAL FIELD

The present invention relates to thiophene containing compounds, compositions comprising such compounds, and methods of treating conditions and disorders using such compounds and compositions.

BACKGROUND (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Accordingly, the need exists to further explore and develop $CB_2$ receptor ligands that exhibit immunomodulatory and anti-inflammatory properties. These $CB_2$ receptors ligands will offer a unique pharmacotherapy for the treatment of immune and inflammatory disorders.

SUMMARY

The present invention generally provides thiophene containing compounds and pharmaceutical compositions and methods for the treatment of disorders using these compounds and pharmaceutical compositions.

In one embodiment, the present invention provides compounds of formula (I), or a pharmaceutically suitable salt or prodrug thereof,

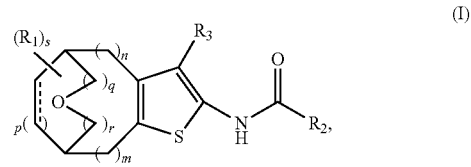

wherein
 ----- is absent or is a bond;
 m, n are each independently 0, 1 or 2;
 p is 1 or 2;
 q and r are each independently 0 or 1;
 s is 0, 1, 2, 3, or 4;
 $R_1$ is selected from the group consisting of alkyl, alkoxyalkyl, alkylcarbonyl, cyano, cyanoalkyl, halo, haloalkyl, $R_4O_2C$—, $R_cR_dNC(O)$—, and $R_cR_dNS(O)_2$—;
 $R_2$ is selected from the group consisting of aryl, cycloalkyl, heteroaryl, heterocycle, —$O(R_h)$, and $R_eR_fN$—;
 $R_3$ is selected from the group consisting of alkyl, alkoxyalkyl, haloalkyl, hydroxyalkyl, $R_5$—C(O)—, $R_5$—C(=N—$OR_p$)—, $R_6OC(O)$—, $R_gR_jNC(O)$—, $R_5$—S(O)$_2$—, and $R_gR_jNS(O)_2$—;
 $R_4$ is selected from the group consisting of alkyl, arylalkyl, haloalkyl, heteroarylalkyl, and heterocyclealkyl;
 $R_5$, at each occurrence, is independently selected from the group consisting of alkyl, alkoxyalkyl, aryl, cycloalkyl, haloalkyl, heteroaryl, and heterocycle;

$R_6$ is selected from the group consisting of alkyl, arylalkyl, haloalkyl, cycloalkyl, cycloalkylalkyl, heterocyclealkyl, and heteroarylalkyl;

$R_c$ and $R_d$, at each occurrence, are each independently selected from the group consisting of hydrogen and alkyl, or $R_c$ and $R_d$ together with the nitrogen atom to which they are attached form a heterocyclic ring;

$R_e$ is selected from the group consisting of hydrogen, alkyl, cycloalkyl, and alkylcarbonyl;

$R_f$ is selected from the group consisting of hydrogen and alkyl;

$R_g$, at each occurrence, is independently selected from the group consisting of hydrogen, alkyl, arylalkyl, cycloalkyl, cycloalkylalkyl, haloalkyl, hydroxyalkyl, alkoxyalkyl, haloalkoxyalkyl, heteroarylalkyl, heterocyclealkyl, and heterocyclealkyl;

$R_j$, at each occurrence, is independently selected from the group consisting of hydrogen, alkyl, and haloalkyl;

$R_h$ is a cycloalkyl ring optionally substituted with 1, 2, 3, 4, 5, or 6 substituents independently selected from the group consisting of alkyl, alkenyl, alkynyl, halogen, hydroxy, alkoxy, haloalkyl, arylalkyl, heteroarylalkyl, cycloalkyl, and heterocyclealkyl; and $R_p$ is selected from the group consisting of hydrogen and alkyl.

In another embodiment, the present invention provides a method for treating pain (for example, neuropathic pain or nociceptive pain) in a mammal in need of such treatment. The method comprises administering to the mammal a therapeutically effective amount of a compound of formula (I) or a pharmaceutically acceptable salt thereof.

In yet another embodiment the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Another embodiment of the present invention relates to a method for providing neuroprotection in a mammal in need of such treatment. The method comprises administering to the mammal a therapeutically effective amount of a compound of formula (I) or a pharmaceutically acceptable salt thereof.

In another embodiment, the present invention provides a pharmaceutical composition comprising a therapeutically effective amount of a compound of the invention or a pharmaceutically acceptable salt thereof in combination with one or more pharmaceutically acceptable carriers. The composition is preferably useful for the treatment of the disease conditions described above.

Further, the present invention provides the use of a compound of formula (I) or a pharmaceutically acceptable salt thereof, in the manufacture of a medicament for the treatment of the disease conditions described above.

These and other objects of the invention are described in the following paragraphs. These objects should not be deemed to narrow the scope of the invention defined by the claims.

DEFINITION OF TERMS

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated from a reaction mixture.

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein.

The term "alkyl" as used herein, means a straight or branched chain saturated hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 1,1-dimethylpropyl, 1,2-dimethylpropyl, 2,3-dimethylpentyl, 1,2,2-trimethylpropyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain saturated hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkylene group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkylene group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl, a bicyclic aryl or a tricyclic aryl. Bicyclic aryls are exemplified by naphthyl, or a phenyl fused to a monocyclic cycloalkyl, or a phenyl fused to a monocyclic cycloalkenyl. Representative examples of the bicyclic aryls include, but are not limited to, dihydroindenyl, indenyl, naphthyl, dihydronaphthalenyl, and tetrahydronaphthalenyl. Tricyclic aryls are exemplied by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracenyl, dihydroanthracenyl, fluorenyl, and tetrahydrophenanthrenyl. The aryl groups of the present invention are attached to the parent molecular moiety through any substitutable carbon atoms within the groups.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, 1-methyl-1-phenylethyl, and 2-naphth-2-ylethyl.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic cycloalkenyl or bicyclic cycloalkenyl. The monocyclic cycloalkenyls are exemplified by cyclic hydrocarbon groups containing from 3 to 10 carbon atoms and at least one carbon-carbon double bond in the ring. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl ring, or a monocyclic cycloalkenyl fused to a monocyclic cycloalkenyl. Representative examples of bicyclic cycloalkenyls include, but are not limited to, 3a,4,5,6,7,7a-hexahydro-1H-indenyl, and 1,2,3,4,5,6-hexahydro-pentalenyl. The cycloalkenyl groups of the present invention are attached to the parent molecular moiety through any substitutable carbon atoms within the groups.

The term "cycloalkyl" as used herein, means a monocyclic cycloalkyl, or a bicyclic cycloalkyl. Monocyclic cycloalkyls are exemplified by a saturated cyclic hydrocarbon group containing from 3 to 8 carbon atoms. Bicyclic cycloalkyls are exemplified by a monocyclic cycloalkyl fused to a monocyclic cycloalkyl. The cycloalkyl groups of the present invention are appended to the parent molecular moiety through any substitutable carbon atom within the group, and may contain one or two alkylene bridges of 1, 2, 3, or 4 carbon atoms wherein each bridge links two non-adjacent carbon atoms within the group. Representative examples cycloalkyl groups include, but are not limited to, cyclopropyl, cyclobutyl, cyclopentyl, cyclohexyl, cycloheptyl, cyclooctyl, adamantyl(tricyclo[3.3.1.1$^{3,7}$]decanyl), noradamantyl(octahydro-2,5-methanopentalene), bicyclo[2.2.2]octyl, bicyclo[3.3.1]nonanyl, bicyclo[2.2.1]heptyl, and bicyclo[3.1.1]heptyl.

The term "cycloalkylalkyl" as used herein, means a cycloalkyl group appended to the parent molecular moiety through an alkylene group, as defined herein. Examples of cycloalkylalkyl include, but are not limited to, cyclopropylmethyl and cyclopropyl-1-methylethyl.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means an haloalkoxy group, as defined herein, appended to the parent molecular moiety through an alkyl group, as defined herein.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2,2,2-trifluoroethyl, trifluoromethyl, 3,3,3-trifluoropropyl, pentafluoroethyl, and 2-chloro-3-fluoropentyl.

The term "heteroaryl" as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three or four heteroatoms in the ring. The 6-membered ring contains three double bonds and one, two, three or four heteroatoms in the ring. Representative examples of monocyclic heteroaryls include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryls are exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl, benzoxadiazolyl, 1,3-benzothiazolyl, benzimidazolyl, benzodioxolyl, benzothiophenyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl. The heteroaryl groups of the present invention are appended to the parent molecular moiety through a substitutable atom within the groups.

The term "heteroarylalkyl" as used herein, means a heteroaryl group appended to the parent molecular moiety through an alkylene group, as defined herein.

The term "heterocycle" or "heterocyclic" as used herein, refers to a monocyclic heterocycle, a bicyclic heterocycle, or a tricyclic heterocycle containing at least one heteroatom. The monocyclic heterocycle is a 3-, 4-, 5-, 6-, 7, or 8-membered ring containing at least one heteroatom independently selected from the group consisting of O, N, and S. The 3- or 4-membered ring contains zero double bond and 1 heteroatom selected from the group consisting of O, N and S. The 5-membered ring contains zero or one double bond and one, two or three heteroatoms selected from the group consisting of O, N and S. The 6-, 7-, or 8-membered ring contains zero, one or two double bonds and one, two or three heteroatoms selected from the group consisting of O, N and S. Representative examples of monocyclic heterocycle include, but are not limited to, azetidinyl, azepanyl, aziridinyl, diazepanyl, 3,4-dihydro-2H-pyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycles of the present invention are exemplified by a monocyclic heterocycle fused to a phenyl group, or a monocyclic heterocycle fused to a monocyclic cycloalkyl, or a monocyclic heterocycle fused to a cycloalkenyl, or a monocyclic heterocycle fused to a monocyclic heterocycle. Representative examples of bicyclic heterocycles include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycles include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl. The heterocycle groups of the present invention are connected to the parent molecular moiety through any substitutable carbon atom or any substitutable nitrogen atom contained within the groups, and may contain one or two alkylene bridges of 1, 2, 3, or 4 carbon atoms, each linking two non-adjacent carbon atoms of the group. Examples of such bridged heterocycle groups include, but are not limited to, 2-oxatricyclo[3.3.1.1$^{3,7}$]decanyl, 2,4-dioxabicyclo[4.2.1]nonanyl, and oxabicyclo[2.2.1]heptyl.

The term "heterocyclealkyl" as used herein, means a heterocycle group appended to the parent molecular moiety through an alkylene group, as defined herein. Non-limiting example heterocyclealkyl includes tetrahydrofuranylmethyl.

The aryl, cycloalkyl, cycloalkenyl, heterocycle, and the heteroaryl groups of the present invention, as a substituent or part of a substituent, are each independently unsubstituted or substituted with 1, 2, 3, 4, 5 or 6 substituents, $R_{101}$, unless otherwise noted. Each $R_{101}$ is independently selected from the group consisting of alkenyl, alkoxy, alkoxyalkoxy, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkoxy, haloalkoxyalkyl, haloalkyl, hydroxy, hydroxyalkyl, mercapto, nitro, oxo, —$NZ_1Z_2$ and ($NZ_3Z_4$)carbonyl.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 2-hydroxypropyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "$NZ_1Z_2$" as used herein, means two groups, $Z_1$ and $Z_2$, which are appended to the parent molecular moiety through a nitrogen atom. $Z_1$ and $Z_2$ are each independently hydrogen, alkyl, alkylcarbonyl, aryl, arylalkyl and formyl. In certain instances within the present invention, $Z_1$ and $Z_2$ taken together with the nitrogen atom to which they are attached form a heterocyclic ring. Representative examples of $NZ_1Z_2$ include, but are not limited to, amino, methylamino, acetylamino, acetylmethylamino, phenylamino, benzylamino, azetidinyl, pyrrolidinyl and piperidinyl.

The term "$NZ_3Z_4$" as used herein, means two groups, $Z_3$ and $Z_4$, which are appended to the parent molecular moiety through a nitrogen atom. $Z_3$ and $Z_4$ are each independently hydrogen, alkyl, aryl, and arylalkyl. Representative examples of $NZ_3Z_4$ include, but are not limited to, amino, methylamino, phenylamino and benzylamino.

The term "$(NZ_3Z_4)$carbonyl" as used herein, means a $NZ_3Z_4$ group, as defined herein, appended to the parent molecular moiety through a carbonyl group, as defined herein. Representative examples of $(NZ_3Z_4)$carbonyl include, but are not limited to, aminocarbonyl, (methylamino)carbonyl, (dimethylamino)carbonyl, and (ethylmethylamino)carbonyl.

The term "oxo" as used herein, means a $=O$ moiety.

The term "sulfinyl" as used herein, means a —S(O)— group.

The term "sulfonyl" as used herein, means a —SO$_2$— group.

It is to be understood that both the foregoing general description and the following detailed description are exemplary, but are not restrictive, of the invention.

DETAILED DESCRIPTION

Compounds of the invention have the formula (I) as described above. Examples of compounds of formula (I) include those wherein m is 0, n is 1, p is 1, q is 0, r is 0, and - - - is absent. Other examples of compounds disclosed of formula (I) include those wherein m is 1, n is 0, p is 1, q is 0, r is 0, and ----- is absent. Yet other examples of compounds of formula (I) include those wherein m is 0, n is 0, p is 1, q is 0, r is 0, and ----- is absent.

It is to be understood that when m is 0, n is 1, p is 1, q is 0, r is 0, and - - - is absent in formula (I), this refers to compounds of formula (Ia)

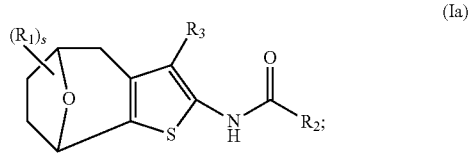

(Ia)

when m is 1, n is 0, p is 1, q is 0, r is 0, and ----- is absent in formula (I), this refers to compounds of formula (Ib)

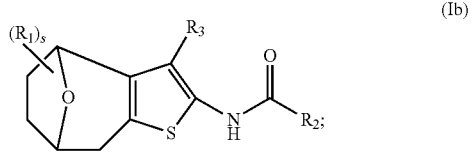

(Ib)

and when m is 0, n is 0, p is 1, q is 0, r is 0, and ----- is absent in formula (I), this refers to compounds of formula (Ic)

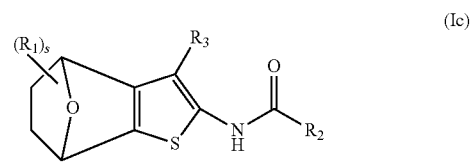

(Ic)

Within each group of examples described hereinabove, s, $R_1$, $R_2$, and $R_3$ have the meanings as defined in the summary section.

Within each group of compounds of formula (I) as described in the preceding paragraphs, examples of a subgroup include those wherein $R_3$ is alkyl, alkoxyalkyl, haloalkyl, or hydroxyalkyl.

Other examples of a subgroup include those wherein $R_3$ is $R_5$—C(O)— and $R_5$ is as defined in the summary section. For example, $R_5$ is cycloalkyl (such as, but not limited to, cyclobutyl), heteroaryl (such as, but not limited to, furanyl), or heterocycle (such as, but not limited to, azetidinyl), wherein each of these rings is independently unsubstituted or substituted as described in the Definition of Terms section. Examples of the optional substituents include, but are not limited to, alkyl, haloalkyl, halogen, and alkoxy.

Other examples of a subgroup include compounds of formula (I) wherein $R_3$ is $R_5$—C(=N—OR$_p$)—, and $R_5$ and $R_p$ are as disclosed in the summary.

Further examples of a subgroup include compounds of formula (I) wherein $R_3$ is $R_6$OC(O)— and $R_6$ is as disclosed in the summary section. For example, $R_6$ is $C_{1-6}$ alkyl. In one embodiment $R_6$ is $C_{1-3}$ alkyl. In yet another embodiment, $R_6$ is ethyl or n-propyl.

Yet further examples of a subgroup include compounds of formula (I) wherein $R_3$ is $R_5$—S(O)$_2$— or $R_gR_jNS(O)_2$—, and $R_5$, $R_g$, and $R_j$ are as defined in the summary section.

Yet other examples of a subgroup include compounds of formula (I) wherein $R_3$ is $R_gR_jNC(O)$—; and $R_g$ and $R_j$ are as disclosed in the summary section. For example, $R_g$ is alkyl (such as methyl, ethyl, n-propyl, and the like), alkoxyalkyl (e.g. 2-methoxyethyl), cycloalkyl (e.g. cyclobutyl, cyclopentyl, and the like), haloalkyl (e.g. 2,2,2-trifluoroethyl, 3,3,3-trifluoropropyl, and the like), hydroxyalkyl (e.g. 2-hydroxyethyl and the like), or heterocyclealkyl (e.g. tetrahydrofuranylmethyl, and the like). $R_j$ is, for example, hydrogen or methyl.

Of all the groups and subgroups of compounds of formula (I) as described in the preceding paragraphs, one embodiment is directed to compounds of formula (I) wherein $R_2$ is aryl, cycloalkyl, or heteroaryl, each of which is independently unsubstituted or substituted as described in the Definition of Terms. For example, $R_2$ is unsubstituted or substituted phenyl. Further examples of $R_2$ are cyclopropyl and octahydro-2,5-methanopentalene, each of which is independently unsubstituted or substituted. Yet another example of $R_2$ is unsubstituted or substituted isoquinolinyl. Examples of the optional substituents of $R_2$ include, but are not limited to, alkoxy (e.g. methoxy, ethoxy, and the like), alkyl (e.g. methyl, isopropyl, and the like), halogen (fluoro, chloro, and the like), haloalkyl (e.g. trifluoromethyl, and the like), and haloalkoxy (e.g. trifluoromethoxy, and the like). Another embodiment is directed to compounds of formula (I) wherein $R_2$ is —O(R$_h$) or NR$_e$R$_f$, and R$_h$, R$_e$ and R$_f$ are as disclosed in the summary section. For example $R_2$ is —O(cyclohexyl) wherein the cyclohexyl moiety is optionally substituted as described in the summary section. Examples of R$_e$ include, but are not limited to, alkyl (e.g. 1,1-dimethylpropyl, 1,2,2-trimethylpropyl, 1,2-dimethylpropyl, and the like) and cycloalkyl (e.g. cyclopentyl). $R_f$ is, for example, hydrogen.

Representative examples of compounds of formula (I) include, but are not limited to:

ethyl 2-{[(2,2,3,3-tetramethylcyclopropyl)carbonyl]amino}-5,6,7,8-tetrahydro-4H-5,8-epoxycyclohepta[b]thiophene-3-carboxylate;

ethyl 2-{[2-fluoro-6-(trifluoromethyl)benzoyl]amino}-5,6,7,8-tetrahydro-4H-5,8-epoxycyclohepta[b]thiophene-3-carboxylate;

ethyl 2-[(hexahydro-2,5-methanopentalen-3a(1H)-ylcarbonyl)amino]-5,6,7,8-tetrahydro-4H-5,8-epoxycyclohepta[b]thiophene-3-carboxylate;

N-{3-[(3,3-difluoroazetidin-1-yl)carbonyl]-5,6,7,8-tetrahydro-4H-5,8-epoxycyclohepta[b]thien-2-yl}-2-fluoro-6-(trifluoromethyl)benzamide;

N-[3-(azetidin-1-ylcarbonyl)-5,6,7,8-tetrahydro-4H-5,8-epoxycyclohepta[b]thien-2-yl]-2-fluoro-6-(trifluoromethyl)benzamide;

2-fluoro-N-{3-[(3-methoxyazetidin-1-yl)carbonyl]-5,6,7,8-tetrahydro-4H-5,8-epoxycyclohepta[b]thien-2-yl}-6-(trifluoromethyl)benzamide;

2-{[2-fluoro-6-(trifluoromethyl)benzoyl]amino}-N-propyl-5,6,7,8-tetrahydro-4H-5,8-epoxycyclohepta[b]thiophene-3-carboxamide;

N-[3-(cyclobutylcarbonyl)-5,6,7,8-tetrahydro-4H-5,8-epoxycyclohepta[b]thien-2-yl]-2-fluoro-6-(trifluoromethyl)benzamide;

N-cyclobutyl-2-{[2-fluoro-6-(trifluoromethyl)benzoyl]amino}-5,6,7,8-tetrahydro-4H-5,8-epoxycyclohepta[b]thiophene-3-carboxamide;

N-cyclopentyl-2-{[2-fluoro-6-(trifluoromethyl)benzoyl]amino}-5,6,7,8-tetrahydro-4H-5,8-epoxycyclohepta[b]thiophene-3-carboxamide;

2-{[2-fluoro-6-(trifluoromethyl)benzoyl]amino}-N-(2-methoxyethyl)-5,6,7,8-tetrahydro-4H-5,8-epoxycyclohepta[b]thiophene-3-carboxamide;

2-{[2-fluoro-6-(trifluoromethyl)benzoyl]amino}-N-(2,2,2-trifluoroethyl)-5,6,7,8-tetrahydro-4H-5,8-epoxycyclohepta[b]thiophene-3-carboxamide;

2-{[2-fluoro-6-(trifluoromethyl)benzoyl]amino}-N-[(2R)-tetrahydrofuran-2-ylmethyl]-5,6,7,8-tetrahydro-4H-5,8-epoxycyclohepta[b]thiophene-3-carboxamide;

2-{[2-fluoro-6-(trifluoromethyl)benzoyl]amino}-N-[(2S)-tetrahydrofuran-2-ylmethyl]-5,6,7,8-tetrahydro-4H-5,8-epoxycyclohepta[b]thiophene-3-carboxamide;

2-fluoro-N-[3-(2-furoyl)-5,6,7,8-tetrahydro-4H-5,8-epoxycyclohepta[b]thien-2-yl]-6-(trifluoromethyl)benzamide;

N-[3-(cyclobutylcarbonyl)-5,6,7,8-tetrahydro-4H-5,8-epoxycyclohepta[b]thien-2-yl]-N'-(1,1-dimethylpropyl)urea;

N-[3-(cyclobutylcarbonyl)-5,6,7,8-tetrahydro-4H-5,8-epoxycyclohepta[b]thien-2-yl]-N'-cyclopentylurea;

N-[3-(cyclobutylcarbonyl)-5,6,7,8-tetrahydro-4H-5,8-epoxycyclohepta[b]thien-2-yl]-N'-(1,2,2-trimethylpropyl)urea;

ethyl 2-{[2-fluoro-6-(trifluoromethyl)benzoyl]amino}-5,6,7,8-tetrahydro-4H-4,7-epoxycyclohepta[b]thiophene-3-carboxylate;

N-[3-(cyclobutylcarbonyl)-5,6,7,8-tetrahydro-4H-5,8-epoxycyclohepta[b]thien-2-yl]-N'-(1,2-dimethylpropyl)urea;

ethyl 2-[(hexahydro-2,5-methanopentalen-3a(1H)-ylcarbonyl)amino]-5,6,7,8-tetrahydro-4H-4,7-epoxycyclohepta[b]thiophene-3-carboxylate;

N-{3-[(3,3-difluoroazetidin-1-yl)carbonyl]-5,6,7,8-tetrahydro-4H-4,7-epoxycyclohepta[b]thien-2-yl}-2-fluoro-6-(trifluoromethyl)benzamide;

2-{[2-fluoro-6-(trifluoromethyl)benzoyl]amino}-N-propyl-5,6,7,8-tetrahydro-4H-4,7-epoxycyclohepta[b]thiophene-3-carboxamide;

N-{3-[(3,3-difluoroazetidin-1-yl)carbonyl]-5,6,7,8-tetrahydro-4H-4,7-epoxycyclohepta[b]thien-2-yl}hexahydro-2,5-methanopentalene-3a(1H)-carboxamide;

ethyl 2-[({[(1R,2S,5R)-2-isopropyl-5-methylcyclohexyl]oxy}carbonyl)amino]-5,6,7,8-tetrahydro-4H-5,8-epoxycyclohepta[b]thiophene-3-carboxylate;

ethyl 2-{[5-chloro-2-(trifluoromethyl)benzoyl]amino}-5,6,7,8-tetrahydro-4H-5,8-epoxycyclohepta[b]thiophene-3-carboxylate;

ethyl 2-{[3-chloro-2-fluoro-6-(trifluoromethyl)benzoyl]amino}-5,6,7,8-tetrahydro-4H-5,8-epoxycyclohepta[b]thiophene-3-carboxylate;

2-[(hexahydro-2,5-methanopentalen-3a(1H)-ylcarbonyl)amino]-N-propyl-5,6,7,8-tetrahydro-4H-4,7-epoxycyclohepta[b]thiophene-3-carboxamide;

2-[(hexahydro-2,5-methanopentalen-3a(1H)-ylcarbonyl)amino]-N-(3,3,3-trifluoropropyl)-5,6,7,8-tetrahydro-4H-4,7-epoxycyclohepta[b]thiophene-3-carboxamide;

ethyl 2-[(isoquinolin-1-ylcarbonyl)amino]-5,6,7,8-tetrahydro-4H-5,8-epoxycyclohepta[b]thiophene-3-carboxylate;

2-{[2-fluoro-6-(trifluoromethyl)benzoyl]amino}-N-(3,3,3-trifluoropropyl)-5,6,7,8-tetrahydro-4H-5,8-epoxycyclohepta[b]thiophene-3-carboxamide;

N-ethyl-2-{[2-fluoro-6-(trifluoromethyl)benzoyl]amino}-5,6,7,8-tetrahydro-4H-5,8-epoxycyclohepta[b]thiophene-3-carboxamide;

N-cyclopentyl-2-{[2-fluoro-6-(trifluoromethyl)benzoyl]amino}-5,6,7,8-tetrahydro-4H-4,7-epoxycyclohepta[b]thiophene-3-carboxamide;

propyl 2-{[2-fluoro-6-(trifluoromethyl)benzoyl]amino}-5,6,7,8-tetrahydro-4H-5,8-epoxycyclohepta[b]thiophene-3-carboxylate;

2-{[2-fluoro-6-(trifluoromethyl)benzoyl]amino}-N,N-dimethyl-5,6,7,8-tetrahydro-4H-5,8-epoxycyclohepta[b]thiophene-3-carboxamide;

N-{3-[(3-methoxyazetidin-1-yl)carbonyl]-5,6,7,8-tetrahydro-4H-4,7-epoxycyclohepta[b]thien-2-yl}hexahydro-2,5-methanopentalene-3a(1H)-carboxamide;

ethyl 2-[({[(1R,2S,5R)-5-methyl-2-(1-methyl-1-phenylethyl)cyclohexyl]oxy}-carbonyl)amino]-5,6,7,8-tetrahydro-4H-5,8-epoxycyclohepta[b]thiophene-3-carboxylate;

propyl 2-{[2-(trifluoromethyl)benzoyl]amino}-5,6,7,8-tetrahydro-4H-5,8-epoxycyclohepta[b]thiophene-3-carboxylate; and ethyl 2-{[2-(trifluoromethyl)benzoyl]amino}-5,6,7,8-tetrahydro-4H-5,8-epoxycyclohepta[b]thiophene-3-carboxylate.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed hererin may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

ABBREVIATIONS

Abbreviations which have been used in the descriptions of the Schemes and the Examples that follow are: DMSO for dimethylsulfoxide; and HOBt for 1-hydroxybenzotriazole hydrate.

METHODS FOR PREPARING COMPOUNDS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R_e$, $R_f$, $R_g$, $R_j$, $R_1$, $R_2$, $R_3$, $R_5$, $R_6$, m, n, p, q, r, and s have the meanings as set forth in the summary section unless otherwise noted, can be synthesized as shown in Schemes 1-7.

As shown in Scheme 1, compounds of formula (I) can be prepared by treating compounds of formula (1) with compounds of formula (2) wherein X is chloro or —OH under appropriate conditions. For example, compounds of formula (I) can be obtained by stirring an about equimolar mixture of the compounds of formula (2) wherein X is chloro, and compounds of formula (1) in solvents such as chloroform, dichloromethane or tetrahydrofuran, in the presence of a base such as, but not limited to, diisopropylethylamine and at a temperature of about 0° C. to about 40° C. Alternatively, compounds of formula (I) can be prepared by stirring an equimolar mixture of compounds of formula (2) wherein X is —OH and compounds of formula (1), a coupling reagent, optionally a coupling auxiliary, and optionally a base, in a solvent such as, but not limited to, tetrahydrofuran, N,N-dimethylacetamide, N,N-dimethylformamide, dichloromethane, ethyl acetate, or mixtures thereof. Non-limiting examples of coupling reagents are 1,1'-carbonyldiimidazole (CDI), bis(2-oxo-3-oxazolidinyl)phosphinic chloride (BOPC1), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), and O-benzotriazol-1-yl-N,N,N',N'-tetramethyluronium tetrafluoroborate (TBTU). Non-limiting examples of coupling auxiliary are 1-hydroxy-7-azabenzotriazole (HOAT) and 1-hydroxybenzotriazole hydrate (HOBT). Examples of suitable base include, but are not limited to N-methyl morpholine, diisopropylethylamine, pyridine, and the like. The coupling1 reactions can be carried out, for example, at a temperature between about 0° C. to about 65° C., and optionally in a microwave reactor.

Compounds of formula (I) wherein $R_2$ is $R_eR_fN$— can be prepared using general procedures as outlined in Schemes 2-4.

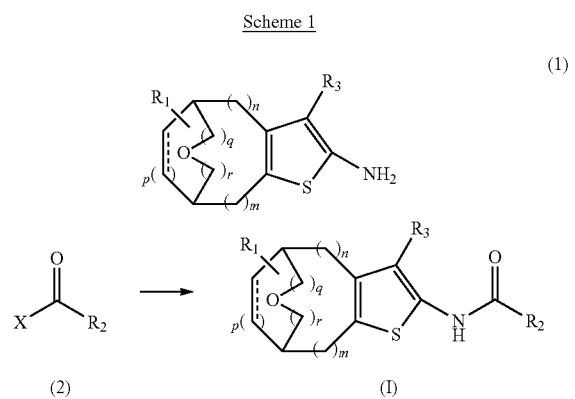

Scheme 1

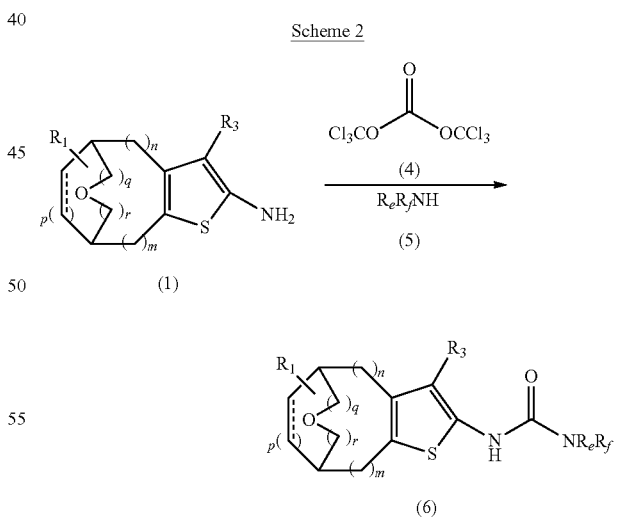

Scheme 2

Compounds of formula (1) when treated with triphosgene of formula (4) in the presence of a base, followed by addition of an amine of formula (5) provide compounds of formula (6). Examples of suitable bases include, but are not limited to, triethylamine and diisopropylethylamine

Scheme 3

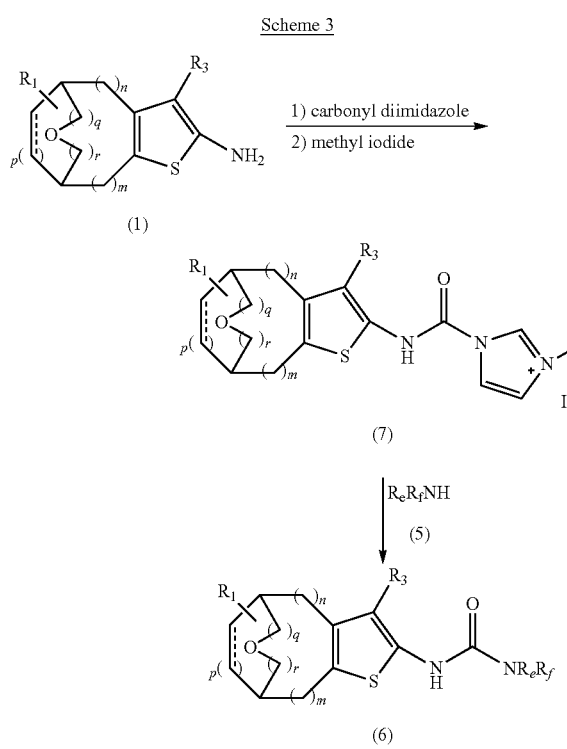

Compounds of formula (6) can be prepared from compounds of formula (1) by (a) treating with 1,1'-carbonyldiimidazole, followed by treatment with methyl iodide, and (b) treating the product from step (a) with an amine of formula (5).

Scheme 4

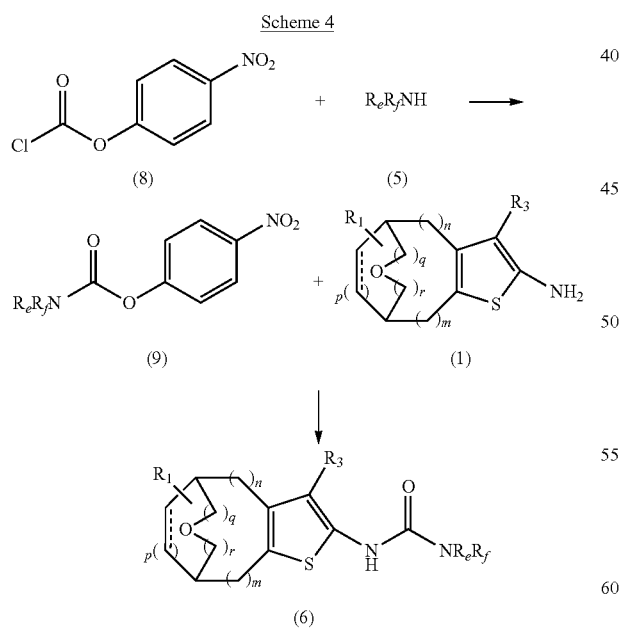

Compounds of formula (6) can also be obtained from (a) reacting compounds of formula (8) with an amine of formula (5), and (b) treating product from step (a) with compounds of formula (1).

Compounds of formula (I) wherein $R_2$ is $NR_eR_f$ and $R_f$ is hydrogen can be synthesized using general procedures as shown in Scheme 5

Scheme 5

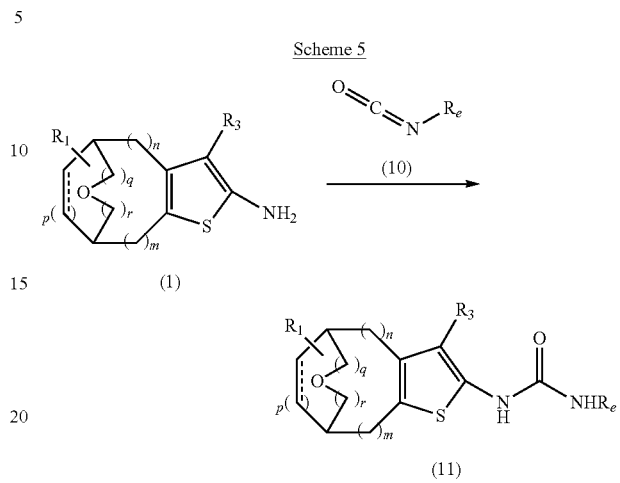

Compounds of formula (1) when treated with an isocyanate of formula (10) provide compounds of formula (11).

Scheme 6

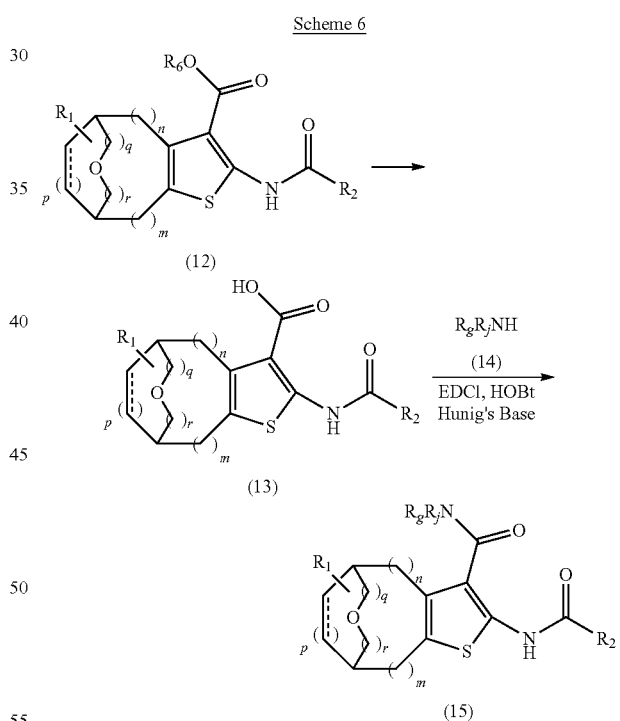

As outlined in Scheme 6, compounds of formula (12) can be hydrolyzed to the corresponding carboxylic acids of formula (13) using reaction conditions known to one skilled in the art. For example, treatment of compounds of formula (12) with sodium, lithium or potassium hydroxide in an aqueous alcoholic solvent such as but not limited to aqueous methanol or ethanol, provide acids of formula (13). Reaction of compounds of formula (13) with amines of formula (14) can be achieved by using reaction conditions as described in Scheme 1.

Scheme 7

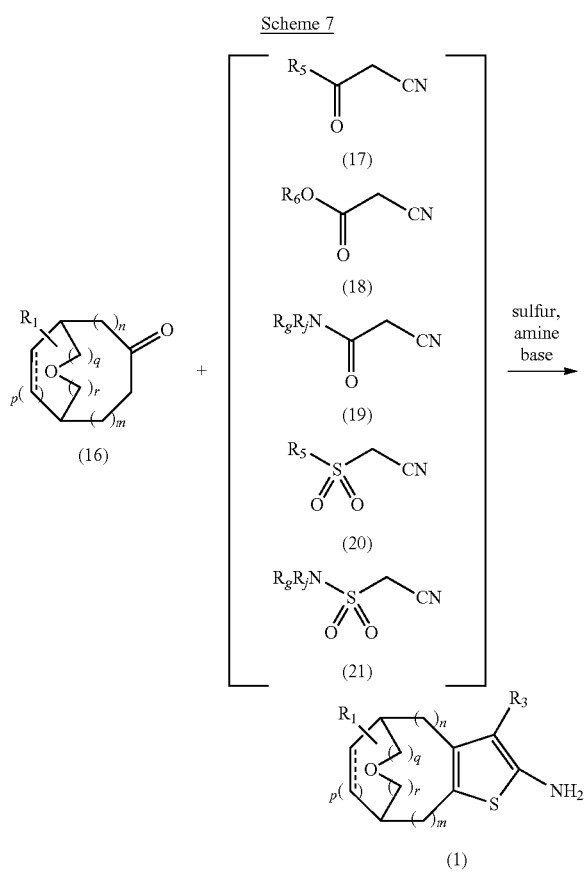

As shown in Scheme 7, compounds of formula (1) wherein $R_3$ is $R_5C(O)-$, $R_{6O}-C(O)-$, $R_gR_jNC(O)-$, $R_5S(O)_2-$ or $R_gR_jNS(O)_2-$, respectively, can be prepared from a Gewald reaction involving the condensation of compounds of formula (16) with compounds of formula (17), (18), (19), (20) or (21), and elemental sulfur, in the presence of about 0.5 to about 1 equivalent of an amine base. The Gewald reaction is typically carried out in a solvent such as, but are not limited to, ethanol, N,N-dimethylformamide or dioxane, at ambient or at elevated temperature. Suitable examples of the amines include, but are not limited to, diethylamine, morpholine or triethylamine. A further review of the chemistry describing the Gewald reaction can be found in *J. Heterocyclic Chem.*, 1999, 36, 333-345, Sabnis, R. W.; Rangnekar, D. W.; Sonawane, N. D.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

EXAMPLES

Example 1 ethyl 2-{[(2,2,3,3-tetramethylcyclopropyl)carbonyl]amino}-5,6,7,8-tetrahydro-4H-5,8-epoxycyclohepta[b]thiophene-3-carboxylate

Example 1A

8-Oxa-bicyclo[3.2.1]octan-3-one

The title compound was prepared according to literature methods described by Ansell, M. F. and Mason, J. S. *J. Chem. Soc., Perkin Trans. I* 1984, 1061-1068.

Example 1B

4-Amino-11-oxa-3-thia-tricyclo[6.2.1.0$^{2,6}$]undeca-2(6),4-diene-5-carboxylic acid ethyl ester To a 50-mL, round-bottomed flask containing a magnetic stir bar were added Example 1A (378 mg, 3.00 mmol), ethyl cyanoacetate (373 mg, 352 μL, 3.30 mmol), and sulfur powder (106 mg, 3.30 mmol). Absolute ethanol (10 mL) was added to form a slurry, and morpholine (393 mg, 393 mL, 4.50 mmol) was added. A reflux condenser with $N_2$ inlet was attached and a heating mantle was applied. The mixture was heated to 60° C. and stirred for 72 hours. The reaction was monitored by LC-MS. After cooling to room temperature, the solvent/volatiles were removed under reduced pressure to provide a brown oil. The product was purified by flash chromatography (silica gel eluting with 25% ethyl acetate in hexanes) to provide the title compound. $^1$H NMR (DMSO-$d_6$, 300 MHz) δ 1.23 (t, J=7.1 Hz, 3H), 1.55-1.65 (m, 1H), 1.88-1.96 (m, 2H), 1.96-2.10 (m, 1H), 2.42 (J=17.3 Hz, 1H), 2.96 (dd, J=17.1, 4.9 Hz, 1H), 4.13 (q, J=7.1 Hz, 2H), 4.57-4.62 (m, 1H), 4.81-4.83 (m, 1H), 7.22 (br s, 2H). MS (ESI$^+$) m/z 254 (M+H)$^+$.

Example 1C ethyl 2-{[(2,2,3,3-tetramethylcyclopropyl)carbonyl]amino}-5,6,7,8-tetrahydro-4H-5,8-epoxycyclohepta[b]thiophene-3-carboxylate To a 20-mL scintillation vial containing a magnetic stir bar were added Example 1B (50 mg, 0.20 mmol), anhydrous tetrahydrofuran (2 mL), and triethylamine (101 mg, 139 μL, 1.00 mmol). 2,2,3,3-Tetramethyl-cyclopropanecarbonyl chloride (48 mg, 0.30 mmol) (prepared from commercially available 2,2,3,3-tetramethyl-cyclopropanecarboxylic acid and thionyl chloride) was dissolved in a few drops of anhydrous tetrahydrofuran and added to the mixture. A fine white precipitate formed immediately. The mixture was stirred at room temperature overnight. The reaction was monitored by LC-MS. A saturated sodium bicarbonate solution (10 mL) was added and the mixture was extracted with dichloromethane (3×8 mL). The combined organic extracts were dried over magnesium sulfate, filtered, and concentrated under reduced pressure to provide a brown oil. The product was purified by flash chromatrography (silica gel 25% ethyl acetate in hexanes) to provide the title compound. $^1$H NMR (DMSO-$d_6$, 300 MHz) δ 1.20 (br s, 6H), 1.21 (s, 3H), 1.23 (s, 3H), 1.31 (t, J=7.1 Hz, 3H), 1.53 (s, 1H), 1.55-1.65 (m, 1H), 1.93-2.11 (m, 3H), 2.54 (d, J=17.1 Hz, 1H), 3.07 (dd, J=17.1, 4.9 Hz, 1H), 4.27 (q, J=7.1 Hz, 2H), 4.65-4.69 (m, 1H), 5.04 (d, J=4.1 Hz, 1H), 11.03 (s, 1H). MS (ESI$^+$) m/z 378 (M+H)$^+$. Anal. calcd. for $C_{20}H_{27}NO_4S$: C, 63.63; H, 7.21; N, 3.71. Found: C, 63.80; H, 6.93; N, 3.35.

Example 2 ethyl 2-{[2-fluoro-6-(trifluoromethyl)benzoyl]amino}-5,6,7,8-tetrahydro-4H-5,8-epoxycyclohepta[b]thiophene-3-carboxylate The title compound was prepared according to the procedure outlined in Example 1C, substituting 2-fluoro-6-trifluoromethyl-benzoyl chloride for 2,2,3,3-tetramethyl-cyclopropanecarbonyl chloride. $^1$H NMR (DMSO-$d_6$, 300 MHz) δ1.26 (t, J=7.1 Hz, 3H), 1.61-1.70 (m, 1H), 1.98-2.14 (m, 3H), 2.57 (d, J=17.3 HZ, 1H), 3.09 (dd, J=17.3, 4.8 Hz, 1H), 4.22 (q, J=7.1 Hz, 2H), 4.68-4.72 (m, 1H), 5.13-5.15 (m, 1H), 7.73-7.86 (m, 3H), 11.51 (s, 1H). MS (ESI$^+$) m/z 444 (M+H)$^+$. Anal. calcd. for $C_{20}H_{17}F_4NO_4S$: C, 54.17; H, 3.86; N; 3.16. Found: C, 54.17; H, 3.78; N, 3.13.

Example 3 ethyl 2-[(hexahydro-2,5-methanopentalen-3a(1H)-ylcarbonyl)amino]-5,6,7,8-tetrahydro-4H-5,8-epoxy-cyclohepta[b]thiophene-3-carboxylate The title compound was prepared according to the procedure outlined in Example 1C, substituting noradamantane-3-carbonyl chloride (prepared from commercially available 3-noradamantane carboxylic acid and thionyl chloride) for 2,2,3,3-tetramethyl-cyclopropanecarbonyl chloride. $^1$H NMR (DMSO-$d_6$, 300 MHz) δ 1.30 (t, J=7.1 Hz, 3H), 1.58-1.68 (m, 5H), 1.77-2.10 (m, 9H), 2.34 (br s, 2H), 2.56 (d, J=17.0 Hz, 1H), 2.64 (t, J=6.6 Hz, 1H), 3.08 (dd, J=17.1, 4.9 Hz, 1H), 4.28 (q, J=7.1 Hz, 2H), 4.66-4.70 (m, 1H), 5.09 (d, J=4.4 Hz, 1H), 11.27 (s, 1H). MS (ESI$^+$) m/z 402 (M+H)$^+$.

Example 4

N-{3-[(3,3-difluoroazetidin-1-yl)carbonyl]-5,6,7,8-tetrahydro-4H-5,8-epoxycyclohepta[b]thien-2-yl}-2-fluoro-6-(trifluoromethyl)benzamide Example 4A 4-(2-Fluoro-6-trifluoromethyl-benzoylamino)-11-oxa-3-thia-tricyclo[6.2.1.0$^{2,6}$]undeca-2(6),4-diene-5-carboxylic acid To a 50-mL, round-bottomed flask containing a magnetic stir bar were added Example 2 (554 mg, 1.25 mmol), solid potassium hydroxide pellets (526 mg, 9.38 mmol), and 8 mL of 5:1 ethanol:water. A reflux condenser was attached and a heating mantle was applied. The mixture was heated to reflux and stirred for 1.5 hours. The reaction was monitored by LC-MS. After cooling to room temperature, 1 N aqueous HCl was added to adjusted the pH to 1 and a white precipitate formed. The mixture was extracted with ethyl acetate. The combined organic extracts were dried over magnesium sulfate, filtered, and concentrated under reduced pressure. The residue was washed with ethyl acetate/hexanes to provide the title compound which was used without further purification. LC-MS (ESI$^+$) m/z 416 (M+H)$^+$.

Example 4B

N-{3-[(3,3-difluoroazetidin-1-yl)carbonyl]-5,6,7,8-tetrahydro-4H-5,8-epoxycyclohepta[b]thien-2-yl}-2-fluoro-6-(trifluoromethyl)benzamide To a 20-mL scintillation vial containing a magnetic stir bar were added Example 4A (83 mg, 0.20 mmol), hydroxybenzotriazole (58 mg, 0.30 mmol), and commercially available 3,3-difluoroazetidine hydrochloride (52 mg, 0.40 mmol). Anhydrous dimethylformamide (2 mL) and ethyldiisopropylamine (52 mg, 70 mL, 0.40 mmol) were added. Solid (3-dimethylamino-propyl)-ethyl-carbodiimide hydrochloride (58 mg, 0.30 mmol) was added and the mixture stirred at room temperature overnight. The reaction was monitored by LC-MS. The solvent/volatiles were removed under reduced pressure. The residue was purified by flash chromatography (silica gel 30% ethyl acetate in hexanes) to provide the title compound. $^1$NMR (DMSO-$d_6$, 300 MHz) δ 1.62-1.70 (m, 1H), 1.98-2.14 (m, 3H), 2.29 (J=16.3 Hz, 1H), 2.92 (dd, J=16.4, 4.9 Hz, 1H), 4.35 (t, J=12.6 Hz, 4H), 4.66-4.70 (m, 1H), 5.10-5.12 (m, 1H), 7.71-7.83 (m, 3H), 11.71 (s, 1H). MS (ESI$^+$) m/z 491 (M+H)$^+$. Anal. calcd. for $C_{21}H_{16}F_6N_2O_3S$: C, 51.43; H, 3.29; N, 5.71. Found: C, 50.99; H, 2.98; N, 5.57.

Example 5

N-[3-(azetidin-1-ylcarbonyl)-5,6,7,8-tetrahydro-4H-5,8-epoxycyclohepta[b]thien-2-yl]-2-fluoro-6-(trifluoromethyl)benzamide The title compound was prepared according to the procedure outlined in Example 4B, substituting commercially available azetidine hydrochloride for 3,3-difluoroazetidine hydrochloride. $^1$H NMR (DMSO-$d_6$, 300 MHz) δ 1.57-1.67 (m, 1H), 1.98-2.21 (m, 5H), 2.25 (d, J=16.3 Hz, 1H), 2.88 (dd, J=16.8, 4.9 Hz, 1H), 3.91 (t, J=7.6 Hz, 4H), 4.65-4.69 (m, 1H), 5.08-5.10 (m, 1H), 7.70-7.82 (m, 3H), 11.84 (s, 1H); MS (ESI$^+$) m/z 455 (M+H)$^+$. Anal. calcd. for $C_{21}H_{18}F_4N_2O_3S$: C, 55.50; H, 3.99; N, 6.16. Found: C, 55.38; H, 3.84; N, 6.14.

Example 6

2-fluoro-N-[3-[(3-methoxyazetidin-1-yl)carbonyl]-5,6,7,8-tetrahydro-4H-5,8-epoxycyclohepta[b]thien-2-yl]-6-(trifluoromethyl)benzamide The title compound was prepared according to the procedure outlined in Example 4B, substituting commercially available 3-methoxyazetidine hydrochloride for 3,3-difluoroazetidine hydrochloride. $^1$H NMR (DMSO-$d_6$, 300 MHz) δ 1.58-1.67 (m, 1H), 1.97-2.14 (m, 3H), 2.24 (d, J=16.3 Hz, 1H), 2.88 (dd, J=16.4, 4.9 Hz, 1H), 3.18 (s, 3H), 3.74 (dd, J=10.0, 3.9 Hz, 2H), 4.01-4.10 (m, 2H), 4.14-4.21 (m, 1H), 4.65-4.69 (m, 1H), 5.09-5.10 (m, 1H), 7.70-7.82 (m, 3H), 11.64 (s, 1H). MS (ESI$^+$) m/z 485 (M+H)$^+$. Anal. calcd. for $C_{22}H_{20}F_4N_2O_4S$: C, 54.54; H, 4.16; N, 5.78. Found: C, 54.44; H, 4.17; N, 6.00.

Example 7

2-{[2-fluoro-6-(trifluoromethyl)benzoyl]amino}-N-propyl-5,6,7,8-tetrahydro-4H-5,8-epoxycyclohepta[b]thiophene-3-carboxamide The title compound was prepared according to the procedure outlined in Example 4B, substituting commercially available propylamine for 3,3-difluoroazetidine hydrochloride. $^1$H NMR (DMSO-$d_6$, 300 MHz) δ 0.85 (t, J=7.3 Hz, 3H), 1.42-1.54 (m, 2H), 1.65-1.73 (m, 1H), 1.98-2.13 (m, 3H), 2.43 (d, J=15.9 Hz, 1H), 3.05-3.27 (m, 4H), 4.70-4.74 (m, 1H), 5.13-5.14 (m, 1H), 7.59 (t, J=5.6 Hz, 1H), 7.71-7.84 (m, 3H), 11.88 (s, 1H); MS (ESI$^+$) m/z 457 (M+H)$^+$.

Example 8

N-[3-(cyclobutylcarbonyl)-5,6,7,8-tetrahydro-4H-5,8-epoxycyclohepta[b]thien-2-yl]-2-fluoro-6-(trifluoromethyl)benzamide Example 8A (2-amino-5,6,7,8-tetrahydro-4H-5,8-epoxycyclohepta[b]thien-3-yl)(cyclobutyl)methanone The title compound was prepared from 3-cyclobutyl-3-oxopropanenitrile (prepared by the method described in Dorsch, J. B.; McElvain, S. M. *J. Am. Chem. Soc.* 1932, 54, 2960-2964) and 8-oxabicyclo[3.2.1]octan-3-one (Example 1A) using the procedure described for Example 1B.
LC/MS (ESI$^+$) m/z 264 (M+H)$^+$.

Example 8B

N-[3-(cyclobutylcarbonyl)-5,6,7,8-tetrahydro-4H-5,8-epoxycyclohepta[b]thien-2-yl]-2-fluoro-6-(trifluoromethyl)benzamide The title compound was prepared from Example 8A and commercially available 2-fluoro-6-trifluoromethyl-benzoyl chloride according to the procedure described for Example 1C. $^1$H NMR (DMSO-$d_6$, 300 MHz) δ 1.65-2.27 (m, 9H), 2.57 (d, J=16.3 Hz, 1H), 3.10-3.27 (m, 2H), 3.76-3.86 (m, 1H), 4.71-4.75 (m, 1H), 5.14-5.16 (m, 1H), 7.76-7.89 (m, 3H), 12.43 (br s, 1H); MS (ESI$^+$) m/z 454 (M+H)$^+$. Anal. calcd. for $C_{22}H_{19}F_4NO_3S$: C, 58.27; H, 4.22; N, 3.09. Found: C, 58.02; H, 4.06; N, 3.07.

Example 9

N-cyclobutyl-2-{[2-fluoro-6-(trifluoromethyl)benzoyl]amino}-5,6,7,8-tetrahydro-4H-5,8-epoxycyclohepta[b]thiophene-3-carboxamide The title compound was prepared from Example 4A and commercially available cyclobutylamine according to the procedure described for Example 4B. $^1$H NMR (DMSO-$d_6$, 300 MHz) δ 1.56-1.73 (m, 3H), 1.94-2.21 (m, 8H), 2.41 (d, J=15.9 Hz, 1H), 3.21 (dd, J=16.9, 5.1 Hz, 1H), 4.24-4.37 (m, 1H), 4.70-4.74 (m, 1H), 5.12-5.13 (m, 1H), 7.69-7.83 (m, 3H), 11.72 (br s, 1H); MS (ESI$^+$) m/z 469 (M+H)$^+$. Anal. calcd. for $C_{22}H_{20}F_4N_2O_3S$: C, 56.40; H, 4.30; N, 5.98. Found: C, 56.32; H, 4.32; N, 5.99.

Example 10

N-cyclopentyl-2-{[2-fluoro-6-(trifluoromethyl)benzoyl]amino}-5,6,7,8-tetrahydro-4H-5,8-epoxycyclohepta[b]thiophene-3-carboxamide The title compound was prepared from Example 4A and commercially available cyclopentylamine according to the procedure described for Example 4B. $^1$H NMR (DMSO-$d_6$, 300 MHz) δ1.45-1.86 (m, 9H), 1.96-2.06 (m, 3H), 2.37 (d, J=15.9 Hz, 1H), 3.18 (dd, J=15.9, 5.4 Hz, 1H), 4.09-4.16 (m, 1H), 4.68-4.73 (m, 1H), 5.12-5.13 (m, 1H), 7.54 (d, J=7.1 Hz, 1H), 7.70-7.83 (m, 3H), 11.68 (br s, 1H); MS (ESI$^+$) m/z 483 (M+H)$^+$.

Example 11

2-{[2-fluoro-6-(trifluoromethyl)benzoyl]amino}-N-(2-methoxyethyl)-5,6,7,8-tetrahydro-4H-5,8-epoxycyclohepta[b]thiophene-3-carboxamide The title compound was prepared from Example 4A and commercially available 2-methoxyethylamine according to the procedure described for Example 4B. $^1$H NMR (DMSO-$d_6$, 300 MHz) δ 1.64-1.72 (m, 1H), 1.98-2.13 (m, 3H), 2.42 (d, J=15.9 Hz, 1H), 3.17 (dd, J=16.4, 5.3 Hz, 1H), 3.23 (s, 3H), 3.36-3.34 (m, 4H), 4.70-4.74 (m, 1H), 5.13-5.14 (m, 1H), 7.60 (t, J=5.3 Hz, 1H), 7.72-7.84 (m, 3H), 11.86 (br s, 1H); MS (ESI$^+$) m/z 473 (M+H)$^+$.

Example 12

2-{[2-fluoro-6-(trifluoromethyl)benzoyl]amino}-N-(2,2,2-trifluoroethyl)-5,6,7,8-tetrahydro-4H-5,8-epoxycyclohepta[b]thiophene-3-carboxamide The title compound was prepared from Example 4A and commercially available 2,2,2-trifluoroethylamine hydrochloride according to the procedure described for Example 4B. $^1$H NMR (DMSO-$d_6$, 300 MHz) δ 1.65-1.73 (m, 1H), 1.99-2.14 (m, 3H), 2.36 (d, J=15.9 Hz, 1H), 3.14 (dd, J=15.9, 4.8 Hz, 1H), 3.83-4.17 (m, 2H), 4.71-4.75 (m, 1H), 5.14-5.15 (m, 1H), 7.69-7.83 (m, 3H), 8.38 (t, J=6.4 Hz, 1H), 11.58 (br s, 1H); MS (ESI$^+$) m/z 487 (M+H)$^+$. Anal. calcd. for $C_{20}H_{15}F_7N_2O_3S$: C, 48.39; H, 3.05; N, 5.64. Found: C, 48.06; H, 2.77; N, 5.75.

Example 13

2-{[2-fluoro-6-(trifluoromethyl)benzoyl]amino}-N-[(2R)-tetrahydrofuran-2-ylmethyl]-5,6,7,8-tetrahydro-4H-5,8-epoxycyclohepta[b]thiophene-3-carboxamide The title compound was prepared from Example 4A and commercially available (R)-aminomethyl-2-tetrahydr according to the procedure described for Example 4B. $^1$H NMR (CDCl$_3$, 300 MHz) δ 1.52-1.61 (m, 3H), 1.70-1.79 (m, 1H), 1.87-2.06 (m, 2H), 2.13-2.27 (m, 2H), 2.49 (dd, J=18.3, 14.6 Hz, 1H), 3.21-3.49 (m, 2H), 3.64-3.72 (m, 1H), 3.74-3.82 (m, 1H), 3.84-3.91 (m, 1H), 3.95-4.07 (m, 1H), 4.83-4.88 (m, 1H), 5.12-5.13 (m, 1H), 6.25-6.31 (m, 1H), 7.34-7.40 (m, 1H), 7.53-7.61 (m, 2H), 12.61 (br s, 1H); MS (ESI$^+$) m/z 499 (M+H)$^+$. Anal. calcd. for $C_{23}H_{22}F_4N_2O_4S$: C, 55.42; H, 4.45; N, 5.62. Found: C, 55.25; H, 4.32; N, 5.56.

Example 14

2-{[2-fluoro-6-(trifluoromethyl)benzoyl]amino}-N-[(2S)-tetrahydrofuran-2-ylmethyl]-5,6,7,8-tetrahydro-4H-5,8-epoxycyclohepta[b]thiophene-3-carboxamide The title compound was prepared from Example 4A and commercially available (S)-aminomethyl-2-tetrahydrofuran according to the procedure described for Example 4B. $^1$H NMR (CDCl$_3$, 300 MHz) δ 1.52-1.61 (m, 3H), 1.70-1.79 (m, 1H), 1.87-2.06 (m, 2H), 2.13-2.27 (m, 2H), 2.49 (dd, J=18.3, 14.6 Hz, 1H), 3.21-3.49 (m, 2H), 3.64-3.72 (m, 1H), 3.74-3.82 (m, 1H), 3.84-3.91 (m, 1H), 3.95-4.07 (m, 1H), 4.83-4.88 (m, 1H), 5.12-5.13 (m, 1H), 6.25-6.31 (m, 1H), 7.34-7.40 (m, 1H), 7.53-7.61 (m, 2H), 12.61 (br s, 1H); MS (ESI$^+$) m/z 499 (M+H)$^+$. Anal. calcd. for $C_{23}H_{22}F_4N_2O_4S$: C, 55.42; H, 4.45; N, 5.62. Found: C, 55.13; H, 4.25; N, 5.62.

Example 15

2-fluoro-N-[3-(2-furoyl)-5,6,7,8-tetrahydro-4H-5,8-epoxycyclohepta[b]thien-2-yl]-6-(trifluoromethyl)benzamide Example 15A (2-amino-5,6,7,8-tetrahydro-4H-5,8-epoxycyclohepta[b]thien-3-yl)(2-furyl)methanone The title compound was prepared from commercially available 3-(furan-2-yl)-3-oxopropanenitrile and Example 1A according to the procedure described for Example 1B. LC/MS (ESI$^+$) m/z 276 (M+H)$^+$.

Example 15B 2-fluoro-N-[3-(2-furoyl)-5,6,7,8-tetrahydro-4H-5,8-epoxycyclohepta[b]thien-2-yl]-6-(trifluoromethyl)benzamide The title compound was prepared from the product of Example 15A and commercially available 2-fluoro-6-trifluoromethyl-benzoyl chloride according to the procedure described for Example 1C. $^1$H NMR (CDCl$_3$, 300 MHz) δ 1.63-1.71 (m, 1H), 2.13-2.17 m, 4H), 3.26 (dd, J=16.3, 5.1 Hz, 1H), 4.71 (dd, J=4.9, 4.9 Hz, 1H), 5.14-5.15 (m, 1H), 6.58-6.60 (m, 1H), 7.16-7.17 (m, 1H), 7.35-7.41 (m, 1H), 7.55-7.64 (m, 3H), 11.13 (br s, 1H); MS (ESI$^+$) m/z 466 (M+H)$^+$.

Example 16

N-[3-(cyclobutylcarbonyl)-5,6,7,8-tetrahydro-4H-5,8-epoxycyclohepta[b]thien-2-yl]-N'-(1,1-dimethylpropyl)urea To a 20-mL scintillation vial containing a magnetic stir bar were added the product from Example 8A (263 mg, 1.00 mmol), anhydrous tetrahydrofuran (8 mL), and triethylamine (354 mg, 488 μL, 3.50 mmol), followed by drop-wise addition of a solution of triphosgene (0.35 mmol) in anhydrous tetrahydrofuran (2 mL). The resulting mixture was stirred at room temperature for 2 hours. A 2-mL aliquot of the mixture was removed and placed in a separate scintillation vial containing a magnetic stir bar and neat 2-methylbutan-2-amine (87 mg, 1.00 mmol) was added. The resulting mixture was stirred at room temperature overnight. The solvent and volatiles were removed by rotary evaporatory and the product was purified by flash chromatography (silica gel: 25% ethyl acetate, 75% hexanes—product $R_f$~0.3) to give 42 mg (56%) of the title compound. $^1$H NMR (DMSO-$d_6$, 300 MHz) δ 0.79 (t, J=7.4 Hz, 3H), 1.22 (s, 3H), 1.23 (s, 3H), 1.54-2.30 (m, 12H), 3.13-3.20 (m, 2H), 3.67-3.77 (m, 1H), 4.67-4.70 (m, 1H), 4.95-4.97 (m, 1H), 7.68 (s, 1H), 11.39 (br s, 1H); MS (ESI$^+$) m/z 377 (M+H)$^+$. Anal. calcd. for $C_{20}H_{28}N_2O_3S$: C, 63.80; H, 7.50; N, 7.50. Found: C, 63.65; H, 7.86; N, 7.37.

Example 17

N-[3-(cyclobutylcarbonyl)-5,6,7,8-tetrahydro-4H-5,8-epoxycyclohepta[b]thien-2-yl]-N'-cyclopentylurea The title compound was prepared from Example 8A) and commercially available cyclopentylamine according to the procedure described for Example 16. $^1$H NMR (DMSO-$d_6$, 300 MHz) δ 1.39-1.68 (m, 8H), 1.76-2.28 (m, 10H), 3.14-3.23 (m, 2H), 3.68-3.78 (m, 1H), 3.88-3.99 (m, 1H), 4.68-4.71 (m, 1H), 4.97-4.99 (m, 1H), 7.96 (d, J=4.4 Hz, 1H), 11.47 (br s, 1H); MS (ESI$^+$) m/z 375 (M+H)$^+$. Anal. calcd. for $C_{20}H_{26}N_2O_3S$: C, 64.14; H, 7.00; N, 7.48. Found: C, 63.99; H, 7.29; N, 7.20.

Example 18

N-[3-(cyclobutylcarbonyl)-5,6,7,8-tetrahydro-4H-5,8-epoxycyclohepta[b]thien-2-yl]-N'-(1,2,2-trimethylpropyl)urea The title compound was prepared from Example 8A and commercially available 3,3-dimethylbutan-2-amine according to the procedure described for Example 16. $^1$H NMR (DMSO-d$_6$, 300 MHz) δ 0.87 (s, 9H), 0.99-1.02 (m, 3H), 1.59-2.31 (m, 11H), 3.13-3.22 (m, 1H), 3.51-3.61 (m, 1H), 3.68-3.78 (m, 1H), 4.66-4.70 (m, 1H), 4.97-4.98 (m, 1H), 7.77 (d, J=9.2 Hz, 1H), 11.44 (br s, 1H); MS (ESI$^+$) m/z 391 (M+H)$^+$. Anal. calcd. for C$_{21}$H$_{30}$N$_2$O$_3$S: C, 64.58; H, 7.74; N, 7.17. Found: C, 64.32; H, 8.06; N, 6.94.

Example 19 ethyl 2-{[2-fluoro-6-(trifluoromethyl)benzoyl]amino}-5,6,7,8-tetrahydro-4H-4,7-epoxycyclohepta[b]thiophene-3-carboxylate Example 19A ethyl 2-amino-5,6,7,8-tetrahydro-4H-4,7-epoxycyclohepta[b]thiophene-3-carboxylate Step A To a solution of 8-oxabicyclo[3.2.1]oct-6-en-2-one (3.38 g, 27.2 mmol) (prepared as described in Vogel, et al. *Tetrahedron* 1993, 49 (8), 1649-1664) in 50 mL of ethanol was added Pd/C (10 wt %, 0.34 g). The reaction flask was evacuated and flushed with nitrogen three times. Then a hydrogen balloon was added and the reaction flask was evacuated and flushed with hydrogen three times. The mixture was stirred under an atmosphere of hydrogen at ambient temperature for 16 hours. The mixture was warmed to 45° C. and allowed to stir for 4 hours. The mixture was cooled to ambient temperature, evacuated and back-filled with nitrogen three times, filtered, and concentrated under reduced pressure. Purification by chromatography (SiO$_2$, 50% hexanes in ethyl acetate) provided approximately 1:1.5 mixture of the starting material and the title compound.

Step B

To a mixture of the product from Step A (1.19 g, ~9.6 mmol) in 20 mL of ethanol was added ethylcyanoacetate (1.12 mL, 10.5 mmol) and sulfur (0.34 g, 10.5 mmol). To this mixture was added morpholine (1.25 mL, 14.4 mmol) dropwise via syringe. The mixture was warmed to 60° C. and was allowed to stir for 72 hours. The mixture was cooled to ambient temperature, filtered, and concentrated under reduced pressure. The resulting residue was purified on silica gel column chromatography (SiO$_2$, 50% hexanes in ethyl acetate).

Step C

A mixture of the product from Step B (1.37 g, ~5.4 mmol) in ethanol (60 mL) was shaken with 2.6 g Pd/C (5 wt %) under hydrogen (60 psi) and ambient temperature for 30 hours. The mixture was filtered and concentrated under reduced pressure. Purification by column chromatography (SiO$_2$, 50% hexanes in ethyl acetate) provided the title compound (1.21 g, 4.8 mmol, ~88% yield). MS (DCI/NH3) m/z 254 (M+H)$^+$.

Example 19B ethyl 2-{[2-fluoro-6-(trifluoromethyl)benzoyl]amino}-5,6,7,8-tetrahydro-4H-4,7-epoxycyclohepta[b]thiophene-3-carboxylate To a solution of the product of Example 19A (0.32 g, 1.26 mmol) and pyridine (0.41 mL, 5.1 mmol) in CH$_3$CN (10 mL) was added 2-fluoro-6-(trifluoromethyl)-benzoylchloride (0.29 mL, 1.9 mmol). The mixture was warmed to 60° C. and was allowed to stir for 18 hours. The mixture was cooled to ambient temperature, quenched with saturated aqueous NH$_4$Cl and diluted with CH$_2$Cl$_2$ (10 mL). The layers were separated and the aqueous layer was extracted with three 5-mL portions of CH$_2$Cl$_2$. The combined organic extracts were dried over anhydrous Na$_2$SO$_4$, filtered, concentrated under reduced pressure. Purification by column chromatography (SiO$_2$, 60% hexanes in ethyl acetate) provided the title compound (0.38 g, 0.86 mmol, 68% yield). $^1$H NMR (300 MHz, CDCl$_3$) δ ppm 1.37 (t, J=7.1 Hz, 3H), 1.67-1.78 (m, 1H), 2.07-2.30 (m, 3H), 2.42 (dd, J=15.9, 0.7 Hz, 1H), 3.30 (dd, J=16.1, 4.9 Hz, 1H), 4.32 (q, J=7.1 Hz, 2H), 4.77-4.85 (m, 1H), 5.50 (d, J=5.1 Hz, 1H), 7.36-7.44 (m, 1H), 7.54-7.64 (m, 2H), 11.49 (s, 1H); MS (DCI/NH$_3$) m/z 461 (M+H)$^+$; Anal. calculated for C$_{20}$H$_{12}$F$_4$NO$_4$S: Calc: C, 54.17; H, 3.86; N, 3.16. Found: C, 54.08; H, 3.80; N, 3.13.

Example 20

N-[3-(cyclobutylcarbonyl)-5,6,7,8-tetrahydro-4H-5,8-epoxycyclohepta[b]thien-2-yl]-N'-(1,2-dimethylpropyl)urea The title compound was prepared from the product of Example 8A and commercially available racemic 3-methylbutan-2-amine according to the procedure described for Example 16. $^1$H NMR (DMSO-d$_6$, 300 MHz) δ 0.84-0.88 (m, 6H), 1.01 (d, J=6.8 Hz, 3H), 1.59-2.28 (m, 11H), 3.14-3.21 (m, 2H), 3.51-3.58 (m, 1H), 3.68-3.78 (m, 1H), 4.67-4.71 (m, 1H), 4.97-4.99 (m, 1H), 7.82 (d, J=8.5 Hz, 1H), 11.47 (br s, 1H); MS (ESI$^+$) m/z 377 (M+H)$^+$.

Example 21 ethyl 2-[(hexahydro-2,5-methanopentalen-3a(1H)-ylcarbonyl)amino]-5,6,7,8-tetrahydro-4H-4,7-epoxycyclohepta[b]thiophene-3-carboxylate Example 21A hexahydro-2,5-methanopentalene-3a(1H)-carbonyl chloride A solution of noradamantane carboxylic acid (0.25 g, 1.5 mmol) in 5 mL of thionyl chloride was warmed to reflux for 2 hours then cooled to ambient temperature and concentrated under reduced pressure. The residue was diluted with toluene (5 mL) then concentrated under reduced pressure (3×) to afford the title compound.

Example 21B ethyl 2-[(hexahydro-2,5-methanopentalen-3a(1H)-ylcarbonyl)amino]-5,6,7,8-tetrahydro-4H-4,7-epoxycyclohepta[b]thiophene-3-carboxylate To the product of Example 19A (0.35 g, 1.4 mmol) in CH$_3$CN (7 mL) was added pyridine (0.34 mL, 4.1 mmol) followed by a solution of the product of Example 21A (1.5 mmol) in CH$_3$CN (7 mL) via cannula. This mixture was warmed to reflux and was allowed to stir for 4 hours. The reaction mixture was cooled to 70° C. and was stirred for 16 hours. The material was cooled to ambient temperature, quenched with saturated aqueous NH$_4$Cl and diluted with 10 mL of CH$_2$Cl$_2$. The layers were separated and the aqueous layer was extracted three 5-mL portions of CH$_2$Cl$_2$. The combined organic extracts were dried over anhydrous Na$_2$SO$_4$, filtered, and concentrated under reduced pressure. Purification by column chromatography (SiO$_2$, 60% hexanes in ethyl acetate) afforded the title compound (0.43 g, 1.07 mmol, 76% yield). $^1$H NMR (300 MHz, CDCl$_3$) δ 1.39 (t, J=7.1 Hz, 3H), 1.62-1.75 (m, 5H), 1.83-2.25 (m, 9H), 2.33-2.43 (m, 3H), 2.74-2.81 (m, 1H), 3.26 (dd, J=15.8, 4.9 Hz, 1H), 4.35 (q, J=7.1 Hz, 2H), 4.74-4.82 (m, 1H), 5.49 (d, J=5.1 Hz, 1H), 11.38 (s, 1H); MS (DCI/NH$_3$) m/z 402 (M+H)$^+$; Anal. calculated for C$_{22}$H$_{22}$F$_4$NO$_4$S: Calc: C, 65.81; H, 6.78; N, 3.49. Found: C, 65.85; H, 6.87; N, 3.53.

Example 22

N-{3-[(3,3-difluoroazetidin-1-yl)carbonyl]-5,6,7,8-tetrahydro-4H-4,7-epoxycyclohepta[b]thien-2-yl}-2-fluoro-6-(trifluoromethyl)benzamide Example 22A 2-{[2-fluoro-6-(trifluoromethyl)benzoyl]amino}-5,6,7,8-tetrahydro-4H-4,7-epoxycyclohepta[b]thiophene-3-carboxylic acid To a solution of the product of Example 19B (0.36 g, 0.81 mmol) in ethanol (10 mL) was added 40 wt % aqueous KOH (2 mL). This mixture was warmed to reflux for 3 hours, then cooled to ambient temperature and acidified to pH 1 with 1 N aqueous HCl. The mixture was extracted with three 10-mL portions of ethyl acetate and the combined organic extracts were dried over anhydrous Na$_2$SO$_4$, filtered and concentrated under reduced pressure to provide the title compound (0.34 g, 0.81 mmol). MS (DCI/NH$_3$) m/z 416 (M+H)$^+$, 433 (M+NH$_4$)$^+$.

Example 22B

N-{3-[(3,3-difluoroazetidin-1-yl)carbonyl]-5,6,7,8-tetrahydro-4H-4,7-epoxycyclohepta[b]thien-2-yl}-2-fluoro-6-(trifluoromethyl)benzamide To a solution of the product of Example 22A (0.11 g, 0.27 mmol) and diisopropylethylamine (0.1 mL, 0.57 mmol) in tetrahydrofuran (5 mL) was added 3,3-difluoroazetidine hydrochloride (36 mg, 0.29 mmol) followed by O-(7-azabenzotriazole-1-yl)-N,N,N'N'-tetramethyluronium hexafluorophosphate (HATU, 0.11 g, 0.29 mmol). The mixture was stirred at ambient temperature for 4 hours, quenched with saturated aqueous NaHCO$_3$ (5 mL) and diluted with ethyl acetate (5 mL). The layers were separated and the aqueous layer was extracted with three 5-mL portions of ethyl acetate. The combined organic extracts were dried over anhydrous Na$_2$SO$_4$, filtered, and concentrated under reduced pressure. Purification by column chromatography (SiO$_2$, 50% hexanes in ethyl acetate) afforded the title compound (56 mg, 0.11 mmol, 42% yield). $^1$H NMR (300 MHz, CDCl$_3$) δ ppm 1.71-1.82 (m, 1H), 1.97-2.03 (m, 1H), 2.09-2.29 (m, 2H), 2.48 (d, J=16.6 Hz, 1H), 3.28 (dd, J=16.1, 4.9 Hz, 1H), 4.30-4.59 (m, 4H), 4.80-4.86 (m, 1H), 5.10 (d, J=5.4 Hz, 1H), 7.37-7.45 (m, 1H), 7.55-7.65 (m, 2H), 10.08 (s, 1H); MS (DCI/NH$_3$) m/z 491 (M+H)$^+$, 508 (M+NH$_4$)$^+$; Anal. calculated for C$_{21}$H$_{16}$F$_6$N$_2$O$_3$S: Calc: C, 51.43; H, 3.29; N, 5.71. Found: C, 51.80; H, 3.63; N, 5.43.

Example 23

2-{[2-fluoro-6-(trifluoromethyl)benzoyl]amino}-N-propyl-5,6,7,8-tetrahydro-4H-4,7-epoxycyclohepta[b]thiophene-3-carboxamide The product of Example 22A (0.11 g, 0.265 mmol), propylamine (51 μL, 0.29 mmol), diisopropylethylamine (0.1 mL, 0.56 mmol) and O-(7-azabenzotriazole-1-yl)-N,N,N'N'-tetramethyluronium hexafluorophosphate (0.11 g, 0.28 mmol) in tetrahydrofuran (5 mL) were processed as described in Example 22B to provide the title compound (45 mg, 0.10 mmol, 37% yield). $^1$H NMR (300 MHz, CDCl$_3$) δ ppm 0.98 (t, J=7.3 Hz, 3H), 1.57-1.66 (m, 2H), 1.78-1.90 (m, 1H), 2.08-2.17 (m, 1H), 2.18-2.40 (m, 2H), 2.47 (d, J=15.9 Hz, 1H), 3.27-3.45 (m, 3H), 4.80-4.89 (m, 1H), 5.25 (d, J=5.4 Hz, 1H), 5.45 (s, 1H), 7.31-7.42 (m, 1H), 7.51-7.62 (m, 2H), 12.18 (s, 1H); MS (DCI/NH$_3$) m/z 457 (M+H)$^+$, 474 (M+NH$_4$)$^+$; Anal. calculated for C$_{21}$H$_{20}$F$_4$N$_2$O$_3$S: Calc: C, 55.26; H, 4.42; N, 6.14. Found: C, 55.19; H, 4.15; N, 5.97.

Example 24

N-{3-[(3,3-difluoroazetidin-1-yl)carbonyl]-5,6,7,8-tetrahydro-4H-4,7-epoxycyclohepta[b]thien-2-yl}hexahydro-2,5-methanopentalene-3a(1H)-carboxamide Example 24A 2-[(hexahydro-2,5-methanopentalen-3a(1H)-ylcarbonyl)amino]-5,6,7,8-tetrahydro-4H-4,7-epoxycyclohepta[b]thiophene-3-carboxylic acid The product of Example 21B (0.41 g, 1.02 mmol) and KOH (3 mL of a 40% aqueous solution) in ethanol (7 mL) were processed as in Example 22A to provide the title compound (0.38 g, 1.02 mmol, 100% yield). MS (DCI/NH$_3$) m/z 374 (M+H)$^+$, 391 (M+NH$_4$)$^+$.

Example 24B

N-{3-[(3,3-difluoroazetidin-1-yl)carbonyl]-5,6,7,8-tetrahydro-4H-4,7-epoxycyclohepta[b]thien-2-yl}hexahydro-2,5-methanopentalene-3a(1H)-carboxamide The product of Example 24A (0.11 g, 0.29 mmol), 3,3-difluoroazetidine hydrochloride (41 mg, 0.32 mmol), diisopropylethylamine (0.11 mL, 0.65 mmol) and O-(7-azabenzotriazole-1-yl)-N,N,N'N'-tetramethyluronium hexafluorophosphate (0.12 g, 0.31 mmol) in tetrahydrofuran (5 mL) were processed as described in Example 22B to provide the title compound (88 mg, 0.20 mmol, 67% yield). $^1$H NMR (300 MHz, CDCl$_3$) δ ppm 1.59-1.76 (m, 5H), 1.83-2.02 (m, 5H), 2.06-2.23 (m, 4H), 2.37-2.48 (m, 3H), 2.72-2.79 (m, 1H), 3.24 (dd, J=16.1, 4.9 Hz, 1H), 4.37 (q, J=11.6 Hz, 2H), 4.55 (q, J=11.9 Hz, 2H), 4.77-4.83 (m, 1H), 5.12 (d, J=5.8 Hz, 1H), 10.19 (s, 1H); MS (DCI/NH$_3$) m/z 449 (M+H)$^+$, 466 (M+NH$_4$)$^+$; Anal. calculated for C$_{23}$H$_{26}$F$_2$N$_2$O$_3$S: Calc: C, 61.59; H, 5.84; N, 6.25. Found: C, 61.42; H, 5.57; N, 6.17.

Example 25 ethyl 2-[({[(1R,2S,5R)-2-isopropyl-5-methylcyclohexyl]oxy}carbonyl)amino]-5,6,7,8-tetrahydro-4H-5,8-epoxycyclohepta[b]thiophene-3-carboxylate To a 20-mL scintillation vial containing a magnetic stir bar were added the product of Example 1B 203 mg, 0.800 mmol), anhydrous tetrahydrofuran (8 mL), and triethylamine (446 μL, 3.20 mmol), followed by addition of a solution of triphosgene (95.0 mg, 0.320 mmol) in dry tetrahydrofuran (1 mL). The reaction mixture was allowed to stir at room temperature for 2 hours. (−)-menthol (156 mg, 1.00 mmol) was added and the resulting brown slurry was stirred at room temperature overnight. Water (10 mL) was added and the mixture was extracted with dichloromethane (3×10 mL). The combined organic extracts were dried over magnesium sulfate, filtered, and concentrated by rotary evaporator. Purification by flash chromatography (silica gel: 10% ethyl acetate, 90% hexanes, product $R_f$-0.5) gave 261 mg (75%) of the title compound. $^1$H NMR (DMSO-$d_6$, 300 MHz) δ 0.76 (d, J=6.8 Hz, 3H), 0.85-0.91 m., 6H), 1.00-1.15 (m, 2H), 1.29 (t, J=7.1 Hz, 3H), 1.38-1.69 (m, 6H), 1.83-2.11 (m, 6H), 3.02-3.09 (m, 1H), 4.24 (q, J=6.9 Hz, 2H), 4.56-4.69 (m, 2H), 5.07 (br s, 1H), 10.23 (br s, 1H); MS (ESI$^+$) m/z 436 (M+H)$^+$. Anal. calcd. for $C_{23}H_{33}NO_5S$: C, 63.42; H, 7.64; N, 3.22. Found: C, 64.22; H, 7.50; N, 2.66.

Example 26 ethyl 2-{[5-chloro-2-(trifluoromethyl)benzoyl] amino}-5,6,7,8-tetrahydro-4H-5,8-epoxycyclohepta [b]thiophene-3-carboxylate The title compound was prepared from the product of Example 1B and commercially available 5-chloro-2-(trifluoromethyl)benzoyl chloride according to the procedure described for Example 1C. $^1$H NMR (DMSO-$d_6$, 300 MHz) δ 1.28 (t, J=7.1 Hz, 3H), 1.58-1.69 (m, 1H), 1.98-2.14 (m, 2H), 2.55-2.61 (m, 1H), 3.06-3.14 (m, 2H), 4.24 (q, J=7.1 Hz, 2H), 4.68-4.72 (m, 1H), 5.14 (br s, 1H), 7.83-7.98 (m, 3H), 11.38 (br s, 1H); MS (ESI$^+$) m/z 460 (M+H)$^+$. Anal. calcd. for $C_{20}H_{17}ClF_3NO_5S$: C, 52.24; H, 3.73; N, 3.05. Found: C, 52.35; H, 3.36; N, 2.92.

Example 27 ethyl 2-{[3-chloro-2-fluoro-6-(trifluoromethyl)benzoyl]amino}-5,6,7,8-tetrahydro-4H-5,8-epoxycyclohepta[b]thiophene-3-carboxylate The title compound was prepared from the product of Example 1B and commercially available 3-chloro-2-fluoro-6-(trifluoromethyl)benzoyl chloride according to the procedure described for Example 1C. $^1$H NMR (DMSO-$d_6$, 300 MHz) δ 1.26 (t, J=7.1 Hz, 3H), 1.60-1.70 (m, 1H), 1.98-2.14 (m, 3H), 2.57 (D, J=16.6 Hz, 1H), 3.06-3.13 (m, 1H), 4.22 (q, J=7.1 Hz, 2H), 4.68-4.72 (m, 1H), 5.13-5.15 (m, 1H), 7.77 (d, J=9.0 Hz, 1H), 8.01 (dd, J=8.0, 8.0 Hz, 1H), 11.58 (br s, 1H); MS (ESI$^+$) m/z 478 (M+H)$^+$. Anal. calcd. for $C_{20}H_{16}ClF_4NO_4S$: C, 50.27; H, 3.37; N, 2.93. Found: C, 50.64; H, 3.07; N, 2.83.

Example 28

2-[(hexahydro-2,5-methanopentalen-3a(1H)-ylcarbonyl)amino]-N-propyl-5,6,7,8-tetrahydro-4H-4,7-epoxycyclohepta[b]thiophene-3-carboxamide The product of Example 24A (0.115 g, 0.31 mmol), propylamine (60 μL, 0.34 mmol), diisopropylethylamine (0.12 mL, 0.68 mmol) and O-(7-azabenzotriazole-1-yl)-N,N,N'N'-tetramethyluronium hexafluorophosphate (0.12 g, 0.32 mmol) in tetrahydrofuran (6 mL) were processed as described in Example 22B to provide the title compound (70 mg, 0.17 mmol, 55% yield). $^1$H NMR (300 MHz, CDCl$_3$) δ ppm 0.96-1.05 (m, 3H), 1.59-1.71 (m, 6H), 1.74-1.96 (m, 5H), 2.04-2.17 (m, 3H), 2.19-2.33 (m, 2H), 2.37 (s, 2H), 2.42 (d, J=15.9 Hz, 1H), 2.76 (t, J=6.6 Hz, 1H), 3.29 (dd, J=15.9, 4.7 Hz, 1H), 3.35-3.49 (m, 2H), 4.78-4.84 (m, 1H), 5.24 (d, J=5.4 Hz, 1H), 5.38 (t, J=5.1 Hz, 1H), 12.02 (s, 1H); MS (DCI/NH$_3$) m/z 415 (M+H)$^+$, 432 (M+NH$_4$)$^+$; Anal. calculated for $C_{23}H_{30}N_2O_3S$: Calc: C, 66.64; H, 7.29; N, 6.76. Found: C, 66.57; H, 7.43; N, 6.74.

Example 29

2-[(hexahydro-2,5-methanopentalen-3a(1H)-ylcarbonyl)amino]-N-(3,3,3-trifluoropropyl)-5,6,7,8-tetrahydro-4H-4,7-epoxycyclohepta[b]thiophene-3-carboxamide The product of Example 24A (70 mg, 0.19 mmol), 3,3,3-trifluoropropylamine hydrochloride (Oakwood Products, 31 mg, 0.21 mmol), diisopropylethylamine (72 μL, 0.41 mmol) and O-(7-azabenzotriazole-1-yl)-N,N,N'N'-tetramethyluronium hexafluorophosphate (75 mg, 0.20 mmol) in tetrahydrofuran (5 mL) were processed as described in Example 22B to provide the title compound (65 mg, 0.14 mmol, 73% yield). $^1$H NMR (300 MHz, CDCl$_3$) δ ppm 1.62-1.82 (m, 5H), 1.85-1.98 (m, 4H), 2.01-2.34 (m, 5H), 2.33-2.55 (m, 5H), 2.73-2.81 (m, 1H), 3.29 (dd, J=16.1, 4.6 Hz, 1H), 3.69-3.81 (m, 2H), 4.77-4.86 (m, 1H), 5.21 (d, J=5.8 Hz, 1H), 5.66 (t, J=6.4 Hz, 1H), 11.96 (s, 1H); MS (DCI/NH$_3$) m/z 469 (M+H)$^+$, 486 (M+NH$_4$)$^+$; Anal. calculated for $C_{23}H_{27}F_3N_2O_3S$: Calc: C, 58.96; H, 5.81; N, 5.98. Found: C, 59.14; H, 5.83; N, 5.85.

Example 30 ethyl 2-[(isoquinolin-1-ylcarbonyl)amino]-5,6,7,8-tetrahydro-4H-5,8-epoxycyclohepta[b]thiophene-3-carboxylate The title compound was prepared from the product of Example 1B and isoquinoline-1-carbonyl chloride (prepared from commercially available isoquinoline-1-carboxylic acid and thionyl chloride) according to the procedure described for Example 1C. $^1$H NMR (DMSO-$d_6$, 300 MHz) δ 1.39 (t, J=7.1 Hz, 3H), 1.63-1.72 (m, 1H), 1.99-2.16 (m, 3H), 2.64 (d, J=17.3 Hz, 1H), 3.12-3.19 (m, 1H), 4.36 (q, J=7.1 Hz, 2H), 4.71-4.75 (m, 1H), 5.16-5.18 (m, 1H), 7.83-7.94 (m, 2H), 8.14-8.17 (m, 1H), 8.24 (d, J=5.4 Hz, 1H), 8.73 (d, J=5.4 Hz, 1H), 9.52 (d, J=8.1 Hz, 1H), 13.17 (br s, 1H); MS (ESI$^+$) m/z 409 (M+H)$^+$. Anal. calcd. for $C_{22}H_{20}N_2O_4S$: C, 64.69; H, 4.94; N, 6.83. Found: C, 65.01; H, 4.77; N, 6.59.

Example 31

2-{[2-fluoro-6-(trifluoromethyl)benzoyl]amino}-N-(3,3,3-trifluoropropyl)-5,6,7,8-tetrahydro-4H-5,8-epoxycyclohepta[b]thiophene-3-carboxamide The title compound was prepared from the product of Example 4A and commercially available 3,3,3-trifluoropropylamine according to the procedure described for Example 4B. MS (DCI/NH$_3$) m/z 511 (M+H)$^+$.

Example 32

N-ethyl-2-{[2-fluoro-6-(trifluoromethyl)benzoyl] amino}-5,6,7,8-tetrahydro-4H-5,8-epoxycyclohepta [b]thiophene-3-carboxamide The title compound was prepared from the product of Example 4A and ethylamine according to the procedure described for Example 4B. MS (DCI/NH$_3$) m/z 443 (M+H)$^+$.

Example 33

N-cyclopentyl-2-{[2-fluoro-6-(trifluoromethyl)benzoyl]amino}-5,6,7,8-tetrahydro-4H-4,7-epoxycyclohepta[b]thiophene-3-carboxamide The product of Example 22A (0.10 g, 0.24 mmol), cyclopentylamine (26 μL, 0.26 mmol), diisopropylethylamine (92 μL, 0.53 mmol) and O-(7-azabenzotriazole-1-yl)-N,N,N'N'-tetramethyluronium hexafluorophosphate (96 mg, 0.25 mmol) in 7 mL tetrahydrofuran were processed as described in Example 22B to provide the title compound (52 mg, 0.11 mmol, 45% yield). $^1$H NMR (300 MHz, CDCl$_3$) δ ppm 1.41-1.52 (m, 2H), 1.65-1.74 (m, 4H), 1.79-1.90 (m, 1H), 1.96-2.39 (m, 5H), 2.47 (d, J=16.3 Hz, 1H), 3.33 (dd, J=16.3, 4.7 Hz, 1H), 4.26-4.37 (m, 1H), 4.81-4.87 (m, 1H), 5.22 (d, J=5.4 Hz, 1H), 5.37-5.42 (m, 1H), 7.31-7.41 (m, 1H), 7.52-7.59 (m, 2H), 12.18 (s, 1H); MS (DCI/NH$_3$) m/z 483 (M+H)$^+$, 500 (M+NH$_4$)$^+$; Anal. calculated for C$_{23}$H$_{22}$F$_4$N$_2$O$_3$S: Calc: C, 57.25; H, 4.60; N, 5.81. Found: C, 57.24; H, 4.42; N, 5.72.

Example 34 propyl 2-{[2-fluoro-6-(trifluoromethyl)benzoyl]amino}-5,6,7,8-tetrahydro-4H-5,8-epoxycyclohepta[b]thiophene-3-carboxylate

Example 34A propyl 2-amino-5,6,7,8-tetrahydro-4H-5,8-epoxycyclohepta[b]thiophene-3-carboxylate The title compound was prepared from propyl cyanoacetate and the product of Example 1A using the procedure described for Example 1B. LC/MS (ESI$^+$) m/z 268 (M+H)$^+$.

Example 34B propyl 2-{[2-fluoro-6-(trifluoromethyl)benzoyl]amino}-5,6,7,8-tetrahydro-4H-5,8-epoxycyclohepta[b]thiophene-3-carboxylate The title compound was prepared from the product of Example 34A and commercially available 2-fluoro-6-trifluoromethyl-benzoyl chloride according to the procedure described for Example 1C. $^1$H NMR (DMSO-d$_6$, 300 MHz) δ0.92 (t, J=7.1 Hz, 3H), 1.60-1.72 (m, 3H), 1.98-2.17 (m, 3H), 2.57 (d, J=17.0 Hz, 1H), 3.10 (dd, J=17.1, 4.9 Hz, 1H), 4.15 (t, J=6.4 Hz, 2H), 4.69-4.73 (m, 1H), 5.14-5.16 (m, 1H), 7.73-7.87 (m, 3H), 11.53 (br s, 1H); MS (ESI$^+$) m/z 458 (M+H)$^+$. Anal. calcd. for C$_{21}$H$_{19}$F$_4$NO$_4$S: C, 55.14; H, 4.19; N, 3.06. Found: C, 55.19; H, 3.99; N, 3.08.

Example 35

2-{[2-fluoro-6-(trifluoromethyl)benzoyl]amino}-N,N-dimethyl-5,6,7,8-tetrahydro-4H-5,8-epoxycyclohepta[b]thiophene-3-carboxamide The title compound was prepared from the product of Example 4A and dimethylamine according to the procedure described for Example 4B. MS (DCI/NH$_3$) m/z 443 (M+H)$^+$.

Example 36

N-{3-[(3-methoxyazetidin-1-yl)carbonyl]-5,6,7,8-tetrahydro-4H-4,7-epoxycyclohepta[b]thien-2-yl}hexahydro-2,5-methanopentalene-3a(1H)-carboxamide The product of Example 24A (0.11 g, 0.29 mmol), 3-methoxy-azetidine hydrochloride (40 mg, 0.32 mmol), diisopropylethylamine (0.11 mL, 0.65 mmol) and O-(7-azabenzotriazole-1-yl)-N,N,N'N'-tetramethyluronium hexafluorophosphate (0.12 g, 0.31 mmol) in tetrahydrofuran (5 mL) were processed as described in Example 22B to provide the title compound (72 mg, 0.16 mmol, 56% yield). $^1$H NMR (300 MHz, CD$_3$OD) δ ppm 1.36-1.39 (m, 2H), 1.66-1.77 (m, 3H), 1.85-2.23 (m, 7H), 2.37 (s, 2H), 2.47 (d, J=15.9 Hz, 1H), 2.69-2.76 (m, 1H), 3.14-3.24 (m, 4H), 3.83-3.88 (m, 2H), 3.88-3.99 (m, 2H), 4.21-4.34 (m, 3H), 4.74-4.82 (m, 1H), 5.09 (d, J=5.4 Hz, 1H); MS (DCI/NH$_3$) m/z 443 (M+H)$^+$, 460 (M+NH$_4$)$^+$; Anal. calculated for C$_{24}$H$_{30}$N$_2$O$_4$S.0.3H$_2$O: Calc: C, 64.35; H, 6.88; N, 6.25. Found: C, 64.06; H, 6.81; N, 6.16.

Example 37 ethyl 2-[({[(1R,2S,5R)-5-methyl-2-(1-methyl-1-phenylethyl)cyclohexyl]oxy}-carbonyl)amino]-5,6,7,8-tetrahydro-4H-5,8-epoxycyclohepta[b]thiophene-3-carboxylate The title compound was prepared from the product of Example 1B and (−)-8-phenylmenthol according to the procedure described for Example 25. MS (ESI) m/z 512 (M+H)$^+$.

Example 38 propyl 2-{[2-(trifluoromethyl)benzoyl]amino}-5,6,7,8-tetrahydro-4H-5,8-epoxycyclohepta[b]thiophene-3-carboxylate The title compound was prepared from the product of Example 34A and commercially available 2-trifluoromethyl-benzoyl chloride according to the procedure described for Example 1C. $^1$H NMR (DMSO-d$_6$, 300 MHz) δ 0.92 (t, J=7.5 Hz, 3H), 1.64-1.71 (m, 3H), 1.98-2.15 (m, 3H), 2.58 (d, J=17.0 Hz, 1H), 3.11 (dd, J=16.6, 4.4 Hz, 1H), 4.16 (t, J=6.4 Hz, 2H), 4.69-4.74 (m, 1H), 5.14-5.16 (m, 1H), 7.80-7.94 (m, 4H), 11.40 (br s, 1H); MS (ESI$^+$) m/z 440 (M+H)$^+$. Anal. calcd. for C$_{21}$H$_{20}$F$_3$NO$_4$S: C, 57.40; H, 4.59; N, 3.19. Found: C, 57.44; H, 4.47; N, 3.14.

Example 39 ethyl 2-{[2-(trifluoromethyl)benzoyl]amino}-5,6,7,8-tetrahydro-4H-5,8-epoxycyclohepta[b]thiophene-3-carboxylate The title compound was prepared from the product of Example 1B and commercially available 2-trifluoromethyl-benzoyl chloride according to the procedure described for Example 1C. $^1$H NMR (DMSO-d$_6$, 300 MHz) δ 1.27 (t, J=7.1 Hz, 3H), 1.59-1.69 (m, 1H), 1.98-2.17 (m, 3H), 2.58 (d, J=17.0 Hz, 1H), 3.11 (dd, J=17.1, 4.9 Hz, 1H), 4.24 (q, J=6.9 Hz, 2H), 4.68-4.73 (m, 1H), 5.13-5.15 (m, 1H), 7.78-7.94 (m, 4H), 11.38 (br s, 1H); MS (ESI$^+$) m/z 426 (M+H)$^+$. Anal. calcd. for C$_{20}$H$_{18}$F$_3$NO$_4$S: C, 56.46; H, 4.26; N, 3.29. Found: C, 56.78; H, 4.18; N, 3.30.

BIOLOGICAL DATA

In Vitro Methods

The $CB_1$ and $CB_2$ radioligand binding assays described herein are utilized to determine the selectivity of compounds of the present invention for binding to $CB_2$ relative to $CB_1$ receptors.

Human $CB_2$ Radioligand Binding Assays:

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 µg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 µL/well of cold assay buffer followed by rapid vacuum filtration through a UniFilter-96 GF/C filter plates (pre-soaked in 1 mg/mL BSA for 2 hours). The bound activity was counted in a Top-Count using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding.

Representative compounds of the present invention bound to $CB_2$ receptors with a $K_i$ of less than 1,000 nM, preferably less than 400 nM, more preferably less than 200 nM and, most preferably less than 100 nM.

Human $CB_1$ Radioligand Binding Assay:

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding. Representative compounds of the present invention exhibited 10-folds to 1000-folds weaker binding affinity (higher $K_i$) to $CB_1$ receptors than to $CB_2$ receptors.

These results show that the compounds of the present invention bind preferably to $CB_2$ receptors, and therefore are selective ligands for the $CB_2$ receptor.

In Vivo Methods:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Incisional Model of Postoperative Pain

A skin incision model of postoperative pain was produced using the procedures described in Brennan et al., 1996, Pain, 64, 493. All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Pogrel, J. M. Chung, and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient Analysis of Experimental Observations, Ann. Rev. Pharmocol. Toxicol., 20, p. 441).

Representative compounds of the present invention showed a statistically significant change in paw withdrawal latency versus a saline vehicle at less than about 300 micromoles/kg in the incisional model of postoperative pain. In a more preferred embodiment, compounds of the present invention showed efficacy at less than about 50 micromoles/kg in the incisional model of postoperative pain.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain, 50, 355) was used to evaluate the compounds of the present invention. The left L5 and L6 spinal nerves of the rat were isolated adjacent to the vertebral column and tightly ligated with a 5-0 silk suture distal to the dorsal root ganglia, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. W. Pogrel, J. M. Chung, and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then hold in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient Analysis of Experimental Observations, Ann. Rev. Pharmocol. Toxicol., 20, p. 441). Only rats with a baseline threshold score of less that 4.25 g were used in this study, and animals demonstrating motor deficit were excluded. Tactile allodynia thresholds were also assessed in several control groups, including naive, sham-operated, and saline infused animals a well as in the contralateral paws of nerve-injured rats.

Representative compounds of the present invention showed a statistically significant change in paw withdrawal latency versus a saline vehicle at less than about 300 micromoles/kg in the spinal nerve ligation model of neuropathic pain. In a more preferred embodiment, compounds of the present invention showed efficacy at less than about 50 micromoles/kg in the spinal nerve ligation model of neuropathic pain.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia expresses a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-1ra is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators have utility for the treatment or prophylaxis of cardiovascular disease and the development of myocardial infarction.

The present invention also provides pharmaceutical compositions that comprise compounds of the present invention. The pharmaceutical compositions comprise compounds of the present invention or pharmaceutically acceptable salt thereof, in combination with one or more pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally" as used herein, refers to modes of administration that include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt" as used herein, means salts derived from inorganic or organic acids. The salts can be prepared in situ during the final isolation and purification of compounds of Formula (I) or separately by reacting the free base of a compound of Formula (I) with an inorganic or organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxy-ethansulfonate (isethionate), lactate, malate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of Formula (I), for example, by hydrolysis in blood.

The present invention contemplates compounds of Formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others, are equivalent to the unsolvated forms for the purposes of the invention.

The total daily dose of the compounds of this invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A method for treating a disorder selected from the group consisting of inflammatory disorders, immune disorders, neurological disorders, cancers of the immune system, respiratory disorders, and cardiovascular disorders in a mammal in need thereof, comprising administering to the mammal a therapeutically effective amount of a compound of formula (I)

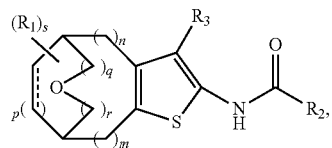

or a pharmaceutically suitable salt or prodrug thereof, wherein

----- is absent or is a bond;
m and n are each independently 0, 1 or 2;
p is 1 or 2;
q and r are each independently 0 or 1;
s is 0, 1, 2, 3, or 4;

$R_1$ is selected from the group consisting of alkyl, alkoxyalkyl, alkylcarbonyl, cyano, cyanoalkyl, halo, haloalkyl, $R_4O_2C-$, $R_cR_dNC(O)-$, and $R_cR_dNS(O)_2-$;

$R_2$ is selected from the group consisting of aryl, cycloalkyl, heteroaryl, heterocycle, $-O(R_h)$, and $R_eR_fN-$;

$R_3$ is selected from the group consisting of alkyl, alkoxyalkyl, haloalkyl, hydroxyalkyl, $R_5-C(O)-$, $R_5-C(=N-OR_p)-$, $R_6OC(O)-$, $R_gR_jNC(O)-$, $R_5-S(O)_2-$, and $R_gR_jNS(O)_2-$;

$R_4$ is selected from the group consisting of alkyl, arylalkyl, haloalkyl, heteroarylalkyl, and heterocyclealkyl;

$R_5$, at each occurrence, is selected from the group consisting of alkyl, alkoxyalkyl, aryl, cycloalkyl, haloalkyl, heteroaryl, and heterocycle;

$R_6$ is selected from the group consisting of alkyl, arylalkyl, haloalkyl, cycloalkyl, cycloalkylalkyl, heterocyclealkyl, and heteroarylalkyl;

$R_c$ and $R_d$, at each occurrence, are each independently selected from the group consisting of hydrogen and alkyl, or $R_c$ and $R_d$ together with the nitrogen atom to which they are attached form a heterocyclic ring;

$R_e$ is selected from the group consisting of hydrogen, alkyl, cycloalkyl, and alkylcarbonyl;

$R_f$ is selected from the group consisting of hydrogen and alkyl;

$R_g$, at each occurrence, is independently selected from the group consisting of hydrogen, alkyl, arylalkyl, cycloalkyl, cycloalkylalkyl, haloalkyl, hydroxyalkyl, alkoxyalkyl, haloalkoxyalkyl, heteroarylalkyl, heterocyclealkyl, and heterocyclealkyl;

$R_j$, at each occurrence, is independently selected from the group consisting of hydrogen, alkyl, and haloalkyl;

$R_h$ is a cycloalkyl ring optionally substituted with 1, 2, 3, 4, 5, or 6 substituents independently selected from the group consisting of alkyl, alkenyl, alkynyl, halogen, hydroxy, alkoxy, haloalkyl, arylalkyl, heteroarylalkyl, cycloalkyl, and heterocyclealkyl; and $R_p$ is selected from the group consisting of hydrogen and alkyl.

* * * * *